US00RE49068E

(19) United States
(12) Reissued Patent
Chambers

(10) Patent Number: US RE49,068 E
(45) Date of Reissued Patent: May 10, 2022

(54) COMPUTER SYSTEM FOR PILL DISPENSING DEVICES

(71) Applicant: R/X Automation Solutions, LLC, Longmont, CO (US)

(72) Inventor: Timothy Chambers, Longmont, CO (US)

(73) Assignee: MCKESSON HIGH VOLUME SOLUTIONS, INC., Irving, TX (US)

(21) Appl. No.: 16/444,957

(22) Filed: Jun. 18, 2019

Related U.S. Patent Documents

Reissue of:
(64) Patent No.: 8,386,275
Issued: Feb. 26, 2013
Appl. No.: 12/703,670
Filed: Feb. 10, 2010

U.S. Applications:
(63) Continuation of application No. 15/895,753, filed on Feb. 13, 2018, now abandoned, which is a (Continued)

(51) Int. Cl.
*G06Q 50/00* (2012.01)
*G07F 11/44* (2006.01)
(Continued)

(52) U.S. Cl.
CPC ..... *G07F 11/44* (2013.01); *A61J 7/02* (2013.01); *G07F 13/025* (2013.01); *G07F 17/0092* (2013.01); *G16H 20/13* (2018.01)

(58) Field of Classification Search
CPC .... G07F 11/44; G07F 13/025; G07F 17/0092; G16H 20/13; A61J 7/02
See application file for complete search history.

(56) References Cited

U.S. PATENT DOCUMENTS 2,109,988 A 3/1938 Dalton
2,111,529 A 3/1938 Dalton
(Continued)

FOREIGN PATENT DOCUMENTS

CA 2560056 6/2009

OTHER PUBLICATIONS

Swiftpack Swiftcheck Plus1 Seed Counter Operating Instructions, Mar. 30, 2000.*
(Continued)

*Primary Examiner* — Jeffrey D Carlson
(74) *Attorney, Agent, or Firm* — Ballard Spahr LLP

(57) ABSTRACT

Devices, systems, and methods for automatic pill dispensing are disclosed herein. An exemplary automatic pill dispensing device includes a temporary storage compartment, a feeding assembly, a dispensing route, a plurality of optical sensors, and a controller. The temporary storage compartment stores pills that are to be counted and eventually dispensed into a pill bottle. The feeding assembly is coupled to the temporary storage compartment and can move or stop the flow of pills into the dispensing route where the plurality of optical sensors count the pills as they pass by the light beams thereof. The controller receives a count from the plurality of optical sensors and stops the feeding assembly when a predetermined count of pills has been reached. Systems and methods utilizing the pill dispensing devices include incorporating a centralized computer and a conveyor belt system to accurately and efficiently dispense a plurality of pill types into pill bottles.

17 Claims, 24 Drawing Sheets

Related U.S. Application Data continuation of application No. 14/633,109, filed on Feb. 26, 2015, now Pat. No. Re. 46,835, which is an application for the reissue of Pat. No. 8,386,275.

(60) Provisional application No. 61/151,483, filed on Feb. 10, 2009.

(51) Int. Cl.

| | |
|---|---|
| ***G16H 20/13*** | (2018.01) |
| ***A61J 7/02*** | (2006.01) |
| ***G07F 13/02*** | (2006.01) |
| ***G07F 17/00*** | (2006.01) |

(56) References Cited

U.S. PATENT DOCUMENTS

| | | | | |
|---|---|---|---|---|
| 3,305,067 | A | 2/1967 | Mayer | |
| 3,730,388 | A | 5/1973 | Bender | |
| 3,837,139 | A | 9/1974 | Roseberg | |
| 3,918,475 | A * | 11/1975 | Trusselle | 141/128 |
| 3,949,792 | A * | 4/1976 | Ramoneda Sibidi | 141/198 |
| 4,013,192 | A | 3/1977 | Dillon | |
| 4,018,358 | A | 4/1977 | Johnson et al. | |
| 4,460,106 | A | 7/1984 | Mouding, Jr. et al. | |
| 4,781,696 | A | 11/1988 | Moulding, Jr et al. | |
| 4,785,952 | A | 11/1988 | Obadia | |
| 5,209,044 | A * | 5/1993 | D'Addario et al. | 53/469 |
| 5,337,919 | A * | 8/1994 | Spaulding et al. | 221/2 |
| 5,460,294 | A | 10/1995 | Williams | |
| 5,480,062 | A | 1/1996 | Rogers et al. | |
| 5,559,919 | A * | 9/1996 | Solberg | 385/92 |
| 5,587,572 | A | 12/1996 | Kirby | |
| 5,720,154 | A | 2/1998 | Lasher et al. | |
| 5,810,198 | A | 9/1998 | Townsend et al. | |
| 5,905,653 | A | 5/1999 | Higham et al. | |
| 5,963,453 | A | 10/1999 | East | |
| 6,006,946 | A | 12/1999 | Williams et al. | |
| 6,036,812 | A | 3/2000 | Williams et al. | |
| 6,053,302 | A | 4/2000 | Leu | |
| 6,112,502 | A | 9/2000 | Frederick et al. | |
| 6,131,765 | A | 10/2000 | Barry et al. | |
| 6,176,392 | B1 | 1/2001 | William et al. | |
| 6,253,953 | B1 | 7/2001 | Ishizuka | |
| 6,317,648 | B1 | 11/2001 | Sleep et al. | |
| 6,377,648 | B1 | 4/2002 | Culbert | |
| 6,421,584 | B1 | 7/2002 | Norberg et al. | |
| RE37,829 | E | 9/2002 | Charhut et al. | |
| 6,497,342 | B2 | 12/2002 | Zhang et al. | |
| 6,504,387 | B1 | 1/2003 | Shail | |
| 6,561,377 | B1 | 5/2003 | Pearson et al. | |
| 6,594,549 | B2 | 7/2003 | Siegel | |
| 6,597,969 | B2 | 7/2003 | Greenwald et al. | |
| 6,640,159 | B2 | 10/2003 | Holmes et al. | |
| 6,644,504 | B2 | 11/2003 | Yuyama et al. | |
| 6,659,304 | B2 | 12/2003 | Gelster et al. | |
| 6,681,149 | B2 | 1/2004 | William et al. | |
| 6,681,550 | B1 | 1/2004 | Aylward | |
| 6,684,914 | B2 | 2/2004 | Gershman et al. | |
| 6,788,997 | B1 | 9/2004 | Frederick | |
| 6,899,144 | B1 | 5/2005 | Gelster et al. | |
| 6,899,148 | B1 | 5/2005 | Gelster et al. | |
| 6,975,922 | B2 | 12/2005 | Duncan et al. | |
| 6,983,579 | B2 | 1/2006 | Rice et al. | |
| 6,996,455 | B2 | 2/2006 | Eggenberger et al. | |
| 6,997,341 | B2 | 2/2006 | Pearson et al. | |
| 7,006,893 | B2 | 2/2006 | Hart et al. | |
| 7,016,766 | B2 | 3/2006 | William et al. | |
| 7,122,005 | B2 | 10/2006 | Shusterman | |
| 7,124,791 | B2 | 10/2006 | Gelster et al. | |
| 7,139,639 | B2 | 11/2006 | Broussard et al. | |
| 7,175,381 | B2 | 2/2007 | Guerra | |
| 7,185,477 | B2 | 3/2007 | Rice et al. | |
| 7,210,598 | B2 | 5/2007 | Gerold et al. | |
| 7,228,198 | B2 | 6/2007 | Vollm et al. | |
| 7,258,521 | B2 | 8/2007 | Guerra et al. | |
| 7,263,411 | B2 | 8/2007 | Shows et al. | |
| 7,289,879 | B2 | 10/2007 | William et al. | |
| 7,395,214 | B2 | 7/2008 | Shillingburg | |
| RE40,453 | E | 8/2008 | Lasher et al. | |
| 7,412,814 | B2 | 8/2008 | Rice et al. | |
| 7,430,838 | B2 | 10/2008 | Rice et al. | |
| 7,469,820 | B2 | 12/2008 | Rosenbluhm | |
| 7,555,362 | B2 | 6/2009 | Broussard et al. | |
| 7,565,784 | B2 | 7/2009 | Williams et al. | |
| 7,624,894 | B2 | 12/2009 | Gerold et al. | |
| 7,631,670 | B2 | 12/2009 | Gelster et al. | |
| 7,668,618 | B2 | 2/2010 | Szesko et al. | |
| 7,747,345 | B2 | 6/2010 | Ohmura et al. | |
| 7,837,107 | B1 | 11/2010 | Leu et al. | |
| 7,991,507 | B2 | 8/2011 | Llff et al. | |
| 8,025,085 | B2 | 9/2011 | Skaggs et al. | |
| 8,060,248 | B1 | 11/2011 | Boyer et al. | |
| 8,109,066 | B2 | 2/2012 | Leu et al. | |
| 8,275,481 | B2 | 9/2012 | Rice et al. | |
| 8,386,275 | B2 | 2/2013 | Chambers | |
| 8,434,641 | B2 | 5/2013 | Coughlin et al. | |
| 8,423,180 | B1 | 6/2013 | Frederick et al. | |
| 8,607,776 | B2 | 12/2013 | Henkel | |
| 8,694,162 | B2 | 4/2014 | Jaynes | |
| 8,983,655 | B2 | 3/2015 | Braun et al. | |
| 9,072,652 | B1 | 7/2015 | Balasubramanian et al. | |
| 9,073,684 | B2 | 7/2015 | Bailey | |
| 9,372,961 | B1 | 6/2016 | Guthrie et al. | |
| 9,489,492 | B2 | 11/2016 | Rosenbaum | |
| 9,506,903 | B2 | 11/2016 | Guthrie et al. | |
| 9,536,369 | B2 | 1/2017 | Wagner | |
| 9,592,925 | B2 | 3/2017 | Leu et al. | |
| 9,682,016 | B1 | 6/2017 | Balasubramanian et al. | |
| 9,697,335 | B2 | 7/2017 | Joplin | |
| 9,922,171 | B2 | 3/2018 | Mahar et al. | |
| RE46,835 | E | 5/2018 | Chambers | |
| 10,062,455 | B2 | 8/2018 | Mahar et al. | |
| 2001/0002448 | A1 | 5/2001 | Wilson et al. | |
| 2001/0019065 | A1 | 9/2001 | William et al. | |
| 2002/0032582 | A1 | 3/2002 | Feeney et al. | |
| 2002/0070227 | A1 | 6/2002 | Ferruccio | |
| 2002/3179628 | | 12/2002 | Gelster et al. | |
| 2003/0085235 | A1 | 5/2003 | William et al. | |
| 2003/0111484 | A1* | 6/2003 | Pearson et al. | 221/211 |
| 2004/0034447 | A1 | 2/2004 | Vollm | |
| 2004/0045977 | A1 | 3/2004 | William et al. | |
| 2004/0249498 | A1 | 12/2004 | William et al. | |
| 2006/0006190 | A1* | 1/2006 | Janet et al. | 221/211 |
| 2006/0025884 | A1* | 2/2006 | Henkel | 700/216 |
| 2006/0071011 | A1 | 4/2006 | Varvarelis | |
| 2006/0105835 | A1* | 5/2006 | Callahan | 463/25 |
| 2006/0124656 | A1 | 6/2006 | Popovich | |
| 2006/0161293 | A1 | 7/2006 | William et al. | |
| 2006/0259195 | A1 | 11/2006 | Eliuk | |
| 2007/0042906 | A1* | 2/2007 | Pitts et al. | 502/350 |
| 2007/0186514 | A1 | 8/2007 | Vollm et al. | |
| 2007/0205211 | A1 | 9/2007 | Vollm et al. | |
| 2007/0208457 | A1 | 9/2007 | Vollm et al. | |
| 2007/0271001 | A1* | 11/2007 | Ratnakar | 700/236 |
| 2008/0198896 | A1* | 8/2008 | Nair | 374/141 |
| 2008/0283543 | A1 | 11/2008 | Karwacki, Jr. et al. | |
| 2009/0165644 | A1* | 7/2009 | Campbell | 95/25 |
| 2011/0202171 | A1 | 8/2011 | Rosenbaum | |
| 2014/0041750 | A1 | 2/2014 | Davis et al. | |
| 2014/0371901 | A1 | 12/2014 | Rosenbaum | |
| 2016/0122045 | A1 | 5/2016 | Kames et al. | |
| 2016/0129585 | A1 | 5/2016 | Davis et al. | |
| 2017/0024541 | A1 | 1/2017 | Joplin | |
| 2017/0065488 | A1 | 3/2017 | Thach et al. | |
| 2017/0116815 | A1 | 4/2017 | Wagner | |
| 2017/0121113 | A1 | 5/2017 | Wagner et al. | |
| 2018/0082757 | A1 | 3/2018 | Chambers et al. | |

OTHER PUBLICATIONS

U.S. Appl. No. 15/895,753, filed Feb. 13, 2018. First Named Inventor: Chambers.

(56) References Cited

OTHER PUBLICATIONS

U.S. Appl. No. 14/633,109, filed Feb. 26, 2015. First Named Inventor: Chambers.
U.S. Appl. No. 12/703,670, filed Feb. 10, 2010. First Named Inventor: Chambers.
U.S. Appl. No. 61/151,483, filed Feb. 10, 2009. First Named Inventor: Chambers.
Swiftpack Swiftcheck Plus1 Seed Counter Operating Instructions, dated Mar. 30, 2000.*
Quote No. 9114 for EKC—Item 3406 RC—Removable canister style EKC tablet counter dated Apr. 25, 2007 with EKC Electronic Kalish Cell Counter brochure attachment.*
Swiftpack Automation Ltd. "Seed Counter Instruction Manual", Alcester, England. May 2000.*

* cited by examiner

COMPUTER SYSTEM FOR PILL DISPENSING DEVICES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

[The present application] *More than one reissue application has been filed for the reissue of U.S. Pat. No. 8,386,275 B2. The reissue applications are U.S. Reissue patent application Ser. No. 16/444,957 (the present application), filed on Jun. 18, 2019, which is a continuation reissue application of U.S. Reissue patent application Ser. No. 15/895,753, filed on Feb. 13, 2018, now abandoned, which is a continuation reissue application of U.S. Reissue patent application Ser. No. 14/633,109, filed on Feb. 26, 2015, now U.S. Reissue Pat. No. RE46,835 E, issued May 8, 2018, which is a reissue application of U.S. patent application Ser. No. 12/703,670, filed on Feb. 10, 2010, now U.S. Pat. No. 8,386,275 B2, issued Feb. 26, 2013, which* claims priority to U.S. Provisional Patent Application No. 61/151,483 filed Feb. 10, 2009, the full disclosure of which is incorporated herein by reference. The aforementioned provisional patent application has the same title and same named inventor as the present application.

FIELD OF THE INVENTION

The present invention relates generally to dispensing devices. More particularly, the present invention relates to pharmaceutical dispensing devices and methods for dispensing pills.

BACKGROUND

Traditionally prescription drugs are dispensed by licensed pharmacists who manually count out the number of pills pertaining to a particular prescription and place them in an appropriately labeled container. While direct human counting may ensure a relatively high degree of accuracy, particularly if the count of pills is low, the cost of having a highly-educated and trained professional performing the work adds significantly to the consumer's cost for the drug. Moreover, as the count of pills to be manually placed in a container increases, such as a container having 120 or more pills, for instance, the accuracy may actually decrease with direct human counting.

Mail order drug fulfillment companies and other similar pharmacy operations have become popular in the last ten years or so as consumers and health care insurance providers look for ways of cutting the costs of obtaining prescription drugs. Large drug fulfillment facilities can deliver economies of scale that are just not possible at a local pharmacy.

To further become more efficient and competitive, many large mail order pharmacies have removed the pharmacist from the responsibility of actually counting and dispensing drugs. Rather, the pharmacist's primary duty is to verify that the contents of a filled pill container and its associated label are correct. Accordingly, a much larger volume of prescription orders can be processed by a single pharmacist.

To perform the counting operation, some mail order pharmacies use various pill counter and dispensing devices. These devices usually contain a large number of pills in a storage hopper or other large container and selectively dispense a set number into a smaller container, such as a pill bottle. These devices are often set up in banks in automated drug dispensing arrays that are centrally controlled. Typically, the pill bottle is positioned under a dispensing tube or throat of the device often through the use of automation. Once positioned, the appropriate number of pills is dispensed into the pill bottle. The filled pill bottle may then be sent to a pharmacist to verify that the contents match the container's label and match the Doctor's prescription. No further counting is required by the pharmacist at this point (unless something seem unusual) and the accuracy of number of pills is completely dependent on the method used for counting and dispensing.

There are various ways to count small objects, such as pills, including: singulation (e.g., counting each individual pill), and estimating by mass and/or volume. Given that the densities of prescription drugs can and do often vary from pill to pill, the preferred method of counting is usually singulation. Current dispensing devices typically count each pill as it falls down a chute using a set of opposed and aligned sensors. Essentially, as a pill passes in front of a sensing beam extending between the opposed sensors, a count is registered. Once the desired number of pills have counted and dispensed, the device stops dispensing and the container is forwarded to the pharmacist for verification.

Prior art pill dispensing devices are about 87% accurate with the tendency towards over-counting the actual number of pills actually dispensed. As a result, it is not uncommon for prescriptions to be shipped with several extra pills. This can be costly for high volume mail order pharmacies and similar operations when high value drugs are being dispensed. Additionally, dust and particulate that settles on the surface of the sensors can cause the sensors to malfunction and alter the count of pills. If dust, particulate, or other debris causes a prescription to be under dispensed, a mail order pharmacy may incur a significant customer service expense once the consumer realizes the under count error.

If the discrepancies caused by a particular dispensing device that is not operating properly are relatively small (1-15%), a reviewing pharmacist will not likely catch the under or over count during his/her verification review. As such, the malfunctioning device may continue to operate improperly for extended periods of time. Heretofore, the ability to count and dispense pills with a high degree of accuracy in the context of large volume pharmacy operations does not satisfactorily exist.

DETAILED DESCRIPTION

Figure 1:
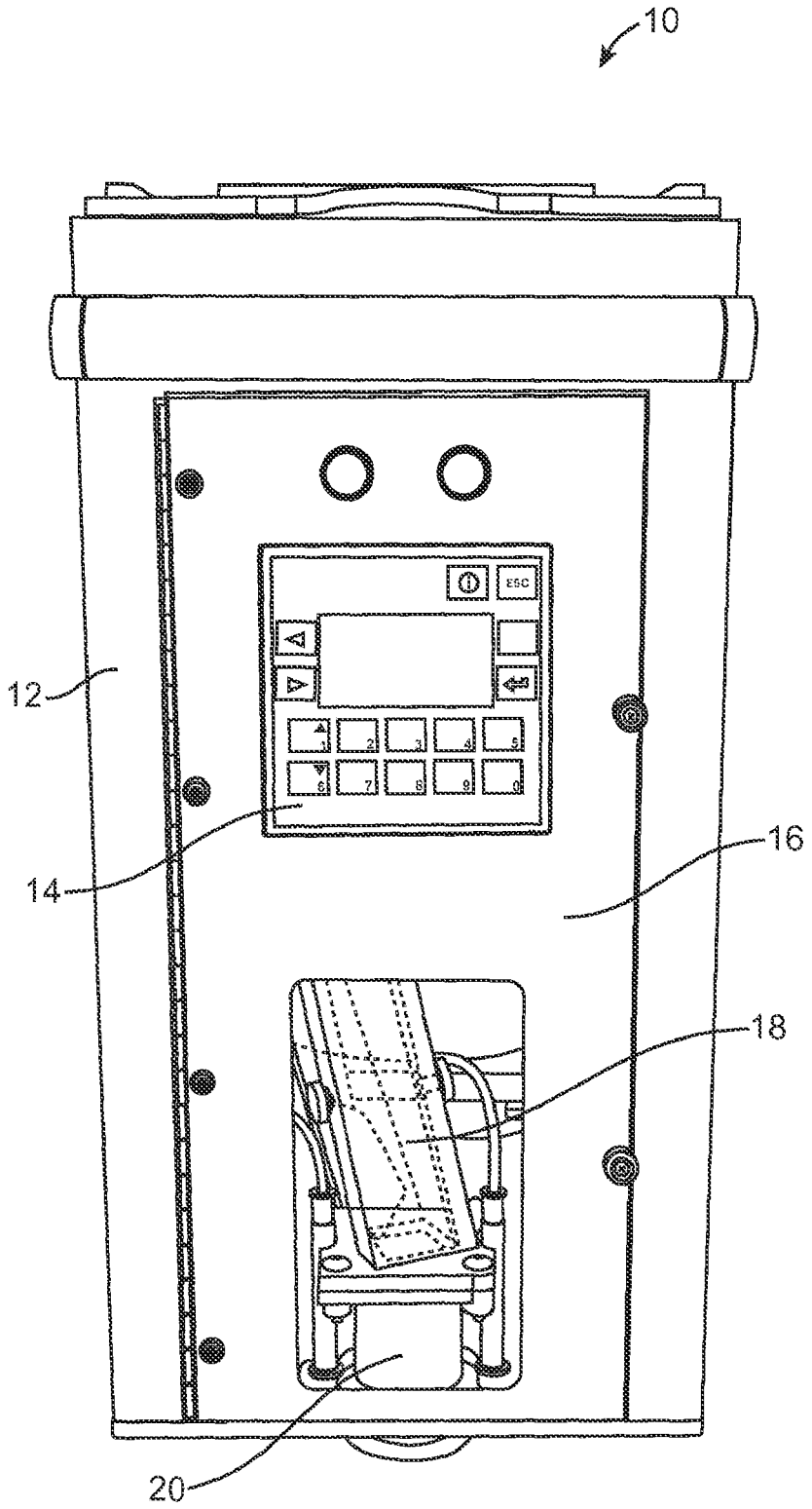
FIG. 1 is a front perspective view of a pill dispensing device according to an embodiment.

Embodiments of the present invention comprise one or more pill dispensing devices as well as methods and systems thereof An exemplary pill dispensing device typically comprises a temporary storage compartment, a feeding assembly, a dispensing route, a plurality of optical sensors, and a controller. Although other components may and usually do exists in various embodiments, these elements generally represent the important aspects of the pill dispensing device.

The temporary storage compartment of the pills dispensing device is adapted to store at least one or more pills, but more typically a plurality of pills in the hundreds or thousands. The pills in the temporary storage compartment are usually of the same type, but variations contemplate implementations whereby a multitude of pill types are included in the temporary storage compartment of the pill dispensing device.

The feeding assembly is coupled to the temporary storage compartment and is adapted to move and stop the pills while in the process of dispensing. The dispensing route is operatively coupled to an exit position of the feeding assembly. In several embodiments, an actually physical or structural coupling of the feeding assembly and the dispensing route need not exist as the pills typically drop from the exit position of the feeding assembly whereby the dispensing route is disposed to receive the pills.

In other embodiments, the dispensing route comprises several portions associated with various operational aspects of the pill dispensing device. For example, the dispensing route can include a dispensing neck. The dispensing neck typically comprises a no-spill dispensing interface between the pill dispensing device and the pill container into which pills are being dispensed. The no-spill dispensing interface typically includes a downwardly extending neck portion that has a mouth adapted to seals up against the rim of a standardized pill bottle to ensure all dispensed pills are properly received in the pill bottle. The dispensing neck may be further adapted to move downwardly against the rim of the bottle to form a seal during the dispensing activity and retract upwardly once the pill bottle is filled so as to not interfere with the operation of a conveyor belt system of other system utilized to rout pill bottle in a facility.

Importantly, embodiments of the pill dispensing device utilizes the plurality of optical sensors and sensor pairs thereof to redundantly count the number of pills associated with a particular prescription that are being dispensed. Each optical sensor of the plurality of optical sensors is adapted to produce a light beam and count the pills as they fall through the dispensing route. The light beam of each optical sensor is disposed within at least a portion of the dispensing route and positioned such that the pills will highly likely, if not almost certainly, pass through the light beam. By counting the number of pills two or more times, the confidence level of the number of pills dispensed increases substantially.

The controller is operatively coupled to the feeding assembly and the plurality of optical sensors to provide various control and commands related to dispensing the pills. For example, the controller receives count signals from the plurality of optical sensors. These count signals include the number of pill that a particular optical sensor has counted. Typically, each time a pill is counted by the particular optical sensor, a new count signal is sent to the controller. Moreover, when certain conditions are met the controller sends a stop instruction to the feeding assembly. Upon receiving the stop instruction, the feeding assembly is adapted to stop moving the pills into the dispensing route.

Other common embodiments of the pill dispensing device further include a housing that encloses a significant portion of the elements and components of the pill dispensing device. The housing typically encloses at least the feeding assembly, a portion of the dispensing route, and the plurality of optical sensors. Generally, at least a portion of the dispensing route extends outside of the housing in order to couple with and dispense into a pill bottle.

It is to be appreciated that the operation of counting and dispensing pills can cause the generation of dust and/or particulate matter within the dispensing device as well as within the pharmaceutical facility. The dust can cause counting problems and inaccuracies to various counting technologies by accumulating on or around a sensor and its circuitry. Moreover, the pill dust and particulate matter can attribute to employee health problems. Therefore, a filtration assembly can be included in embodiments of the pill dispensing device. Since many types of pills emit dust and/or particulate matter, the filtration assembly is adapted to remove air, dust, and/or particulate matter from an interior cavity of the housing as well as the facility in general.

To further minimize dust and particulate matter generation, some embodiments of the pill dispensing device incorporate an HEPA (or near HEPA grade) filtration system that creates a negative pressure environment within the interior cavity of the housing. Such filtration system can mount to the rear of the pill dispensing device and pulls air from within the pill dispensing device during the pill counting and dispensing operation and sometimes shortly thereafter. By creating the negative pressure environment within the pill dispensing device, a substantial amount of any generated pill dust and particulate matter is captured by a filter therein reducing the risk of optical sensor malfunction.

It is to be appreciated that some embodiments of the present invention include processes and methodology for utilizing the one or more pill dispensing devices to increase the accuracy of shipped prescriptions from the current level of approximately 87% too much greater levels, which in certain circumstances can approach 99.7%. When a discrepancy is recorded (e.g., a sensor mismatch, known over-count, or a known undercount), typically but not necessarily by default operation a known over-count, a system for dispensing pills can either route a pill bottle for a given prescription to a final verification station or to a technician station to perform a manual count of the pills in the pill bottle. Consequently, the implementation of this system gives an end user the ability to make certain operational decisions. For example, a manual recount may or may not be justified given the particular situation and/or conditions. The manual recount can be performed by a technician as opposed to a pharmacist. Once the manual recount has been completed the prescription can be placed back into the system and routed to the pharmacist for final verification.

TERMINOLOGY

The terms and phrases as indicated in quotation marks (“ ”) in this section are intended to have the meaning ascribed to them in this Terminology section, applied to them throughout this document, including in the claims, unless clearly indicated otherwise in context. Further, as applicable, the stated definitions are to apply, regardless of the word or phrase’s case, to the singular and plural variations of the defined word or phrase.

The term “or” as used in this specification and the appended claims is not meant to be exclusive; rather the term is inclusive, meaning either or both.

References in the specification to: “one embodiment”; “an embodiment”; “another embodiment”; “an alternative embodiment”; “one variation”; “a variation”; and similar phrases mean that a particular feature, structure, or characteristic described in connection with the embodiment or variation, is included in at least an embodiment or variation of the invention. The phrase “in one embodiment,” “in one variation,” or similar phrases, as used in various places in the specification, are not necessarily meant to refer to the same embodiment or the same variation.

The term “couple” or “coupled,” as used in this specification and the appended claims, refers to either an indirect or direct connection between the identified elements, components or objects. Often the manner of the coupling will be related specifically to the manner in which the two coupled elements interact.

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiments and are not necessarily intended to be construed as limiting.

As applicable, the terms “about” or “generally” as used herein unless otherwise indicated means a margin of +−20%. Also, as applicable, the term “substantially” as used herein unless otherwise indicated means a margin of +−10%. Concerning angular measurements, “about” or “generally” refers to +−10 degrees and “substantially” refers to +−5.0 degrees unless otherwise indicated. It is to be appreciated that not all uses of the above terms are quantifiable such that the referenced ranges can be applied.

The term “pill” as used in this specification and the appended claims, is not restricted to a pill as defined by its method of construction, composition, or shape, but rather refers to any type of a small mass of a substance, typically a medication or dietary preparation to be taken orally. Non-limiting examples of a pill include a tablet, chewable tablet, capsule, gelcap, and caplet.

The term “light beam” as used in this specification and the appended claims, generally refers to one or more rays of light. Light can be any wavelength of electromagnetic radiation comprising one or more of visible light, infrared light, and ultraviolet (UV). The one or more light rays comprising a light beam are typically collimated.

An Exemplary Embodiment of an Automatic Pill Dispensing System

FIG. 1 is a front perspective view of a pill dispensing device 10 according to an embodiment. The pill dispensing device 10 generally includes a housing, a temporary storage compartment, a feeding assembly, a dispensing route, a plurality of optical sensors, a filtration system, and a controller. The housing includes a frame 12 that surrounds a front door panel 16 that is hinged connection therewith. The front door panel 16 includes a window portion through which a dispensing chute 18 and a dispensing neck 20 can be viewed. The dispensing chute 18 and the dispensing neck 20 are section comprising the dispensing route of the pill dispensing device 10.

A controller interface panel 14 is also included and illustrated in FIG. 1. The controller interface panel 14 is coupled to the controller and typically provides a user interface for the pill dispensing device 10. The controller interface panel 14 typically includes a display screen, an entry keypad, and other display and data entry components.

In use, a front edge of the dispensing device 10 typically overhangs a support surface. The pill dispensing device 10 can be mounted and secured to the support surface. Accordingly, the dispensing neck 20 can move downwardly and upwardly (extend and retract) to facilitate interconnection with a pill bottle.

The housing also typically includes one or more panels and fasteners to substantially enclose components and elements of the pill dispensing device. The housing typically encloses the feeding assembly, a portion of the dispensing route, and the plurality of optical sensors. Because the dispensing neck 20 is typically adapted to extend and retract to engage with pill bottles, at least a portion of the dispensing route typically resides beyond the housing. However, it is pertinent to note that the housing is not necessarily required in some embodiments of the pill dispensing device. Alternatively, a larger housing assembly may comprise a plurality of pill dispensing device in some implementations.

Figure 2:
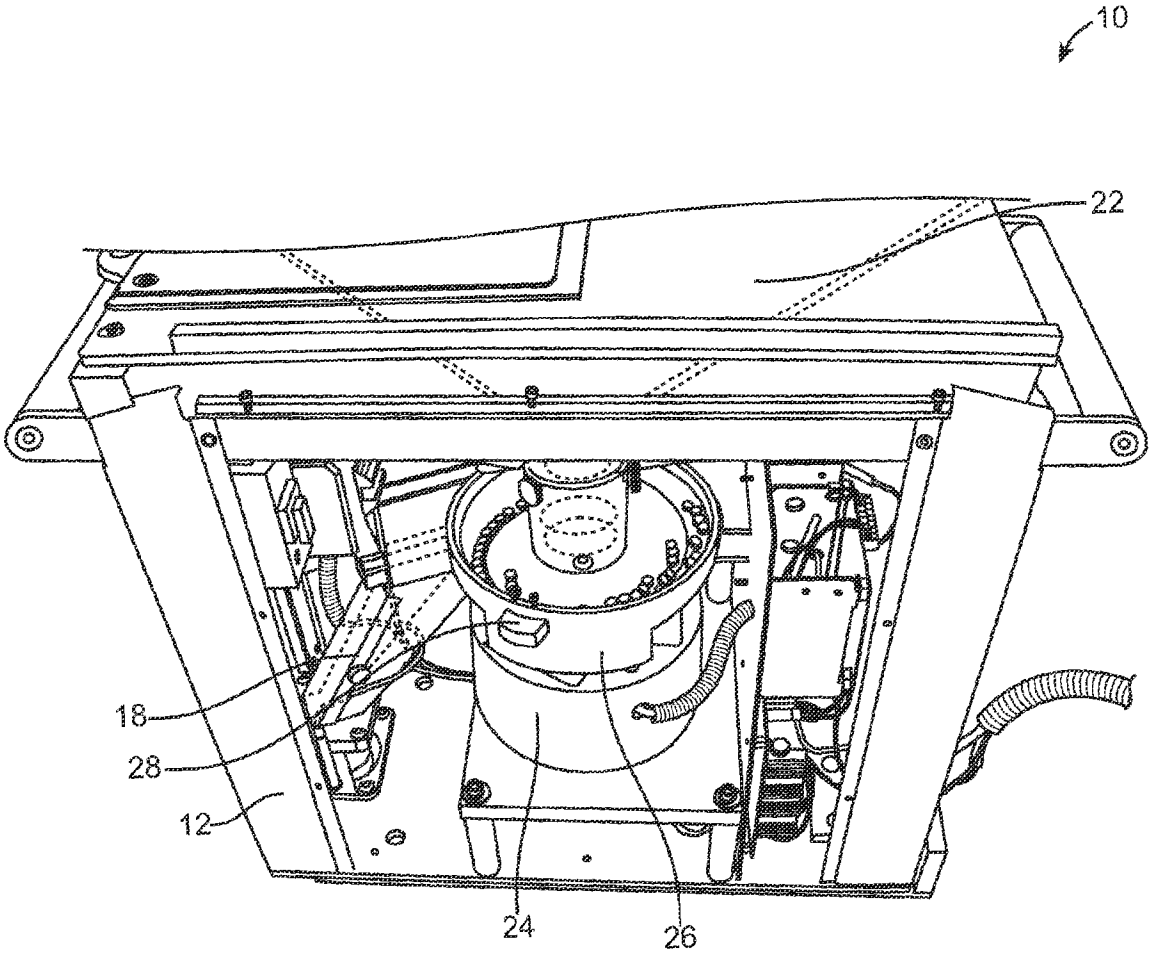
FIG. 2 is a right side perspective view of a pill dispensing device according to an embodiment.

Now referring to FIG. 2, the pill dispensing device 10 is illustrated from the right side with a panel removed from the frame 12. At the top of FIG. 2, a portion of a hopper 22 can be seen. The hopper 22 is utilized as the temporary storage compartment for the pill dispensing device 10. Pills are temporarily stored in the hopper 22, which has a neck that is coupled to the feeding assembly. It is relevant to note that in some variations, the neck of the hopper 22 can comprise a releasing mechanism adapted to control the flow of pills into the feeding assembly. The releasing mechanism may be controlled by the controller or another device or system associated with the pharmaceutical and/or dispensing facility thereby enabling the pills to be metered out at a desired rate into the feeding assembly. Moreover, several hoppers comprising a first stage and a second stage may be utilized as the temporary storage compartment for the pill dispensing device 10.

Next, as can be seen in FIG. 2, the hopper 22 connects to a vibratory feeder bowl 26. The vibratory feeder bowl 26 is operatively coupled with a vibratory base unit 24. The vibratory feeder bowl 26 and the vibratory base unit 24 comprise the feeding assembly of the pill dispensing device 10. In operation, the pills ascend up a spiraling edge of the vibratory feeder bowl 26 to an exit edge by vibratory force. The exit edge represents an exit position from the feeding assembly to the dispensing route in an embodiment. The exit position is typically a point where the pills will free fall after leaving the feeding mechanism. However, implementations where a force is directed to the pill so that it is directed instead of dropping down via gravity are contemplated. In an embodiment, the pills typically fall from the exit edge of the vibratory feeder bowl 26 into the dispensing route (a portion of which, the dispensing chute 18 can be seen in FIG. 2) and eventually a pill bottle. Moreover, the vibratory base unit 24 can be adapted to vibrate at a plurality of speeds. For example, the vibratory base unit 24 may produce a stronger vibratory force at the beginning of a cycle to fulfill a prescription and then produce a softer vibratory force toward the end of the cycle so that additional pills do not fall into the dispensing route after a desired count for the prescription has been achieved.

It is to be appreciated that more than a single pill can fit either side to side on a ledge or one on top of the other. Accordingly, a device known as a singulator 28 is typically provided with and coupled to the vibratory feeder bowl 26 prior to the exit edge. The singulator 28, which will be described in greater detail below acts to ensure only pills that pass by it are moving in single file.

Although the vibratory feeder bowl 26, vibratory base unit 24, and singulator 28 comprise an effective assembly for the feeding assembly of the pill dispensing device, other means to feed pills from the temporary storage compartment and into the dispensing route are contemplated.

Figure 3:
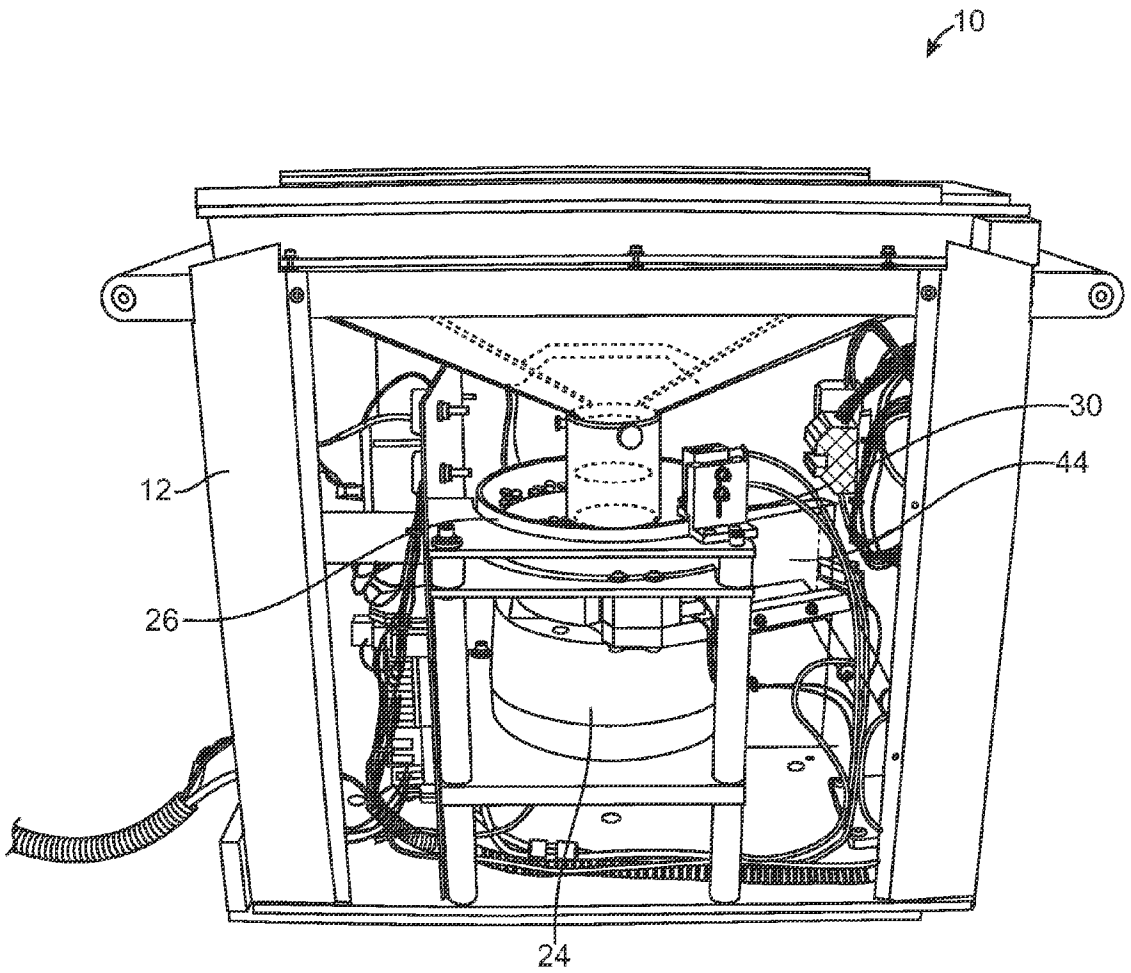
FIG. 3 is a left side perspective view of a pill dispensing device according to an embodiment.

FIG. 3 is a left side perspective view of the pill dispensing device 10 according to an embodiment. The interior of the pill dispensing device 10 is shown from the left side with a panel removed from the frame 12. The feeding assembly further includes a stopping mechanism coupled to the vibratory feeder bowl proximal the exit position as illustrated. The stopping mechanism typically comprises a pneumatic pill stopping mechanism 30. In operation, the pneumatic pill stopping mechanism 30 includes a shoe that extends downwardly against pills located proximal the exit edge of the vibratory feeder bowl 26. When activated, the pneumatic pill stopping mechanism 30 acts to prevent the pills from inadvertently falling over the exit edge once the desired count for the prescription has been achieved and the pill counting/dispensing operation has ceased.

Additionally, an upper portion 44 of the dispensing route can be seen from the left side perspective view of FIG. 3. The upper portion 44 is proximal the pneumatic pill stopping mechanism 30 and the exit edge of the vibratory feeder bowl 26 as well as being the first portion of the dispensing route that the pills enter upon leaving the exit position of the feeding assembly.

Figure 4:
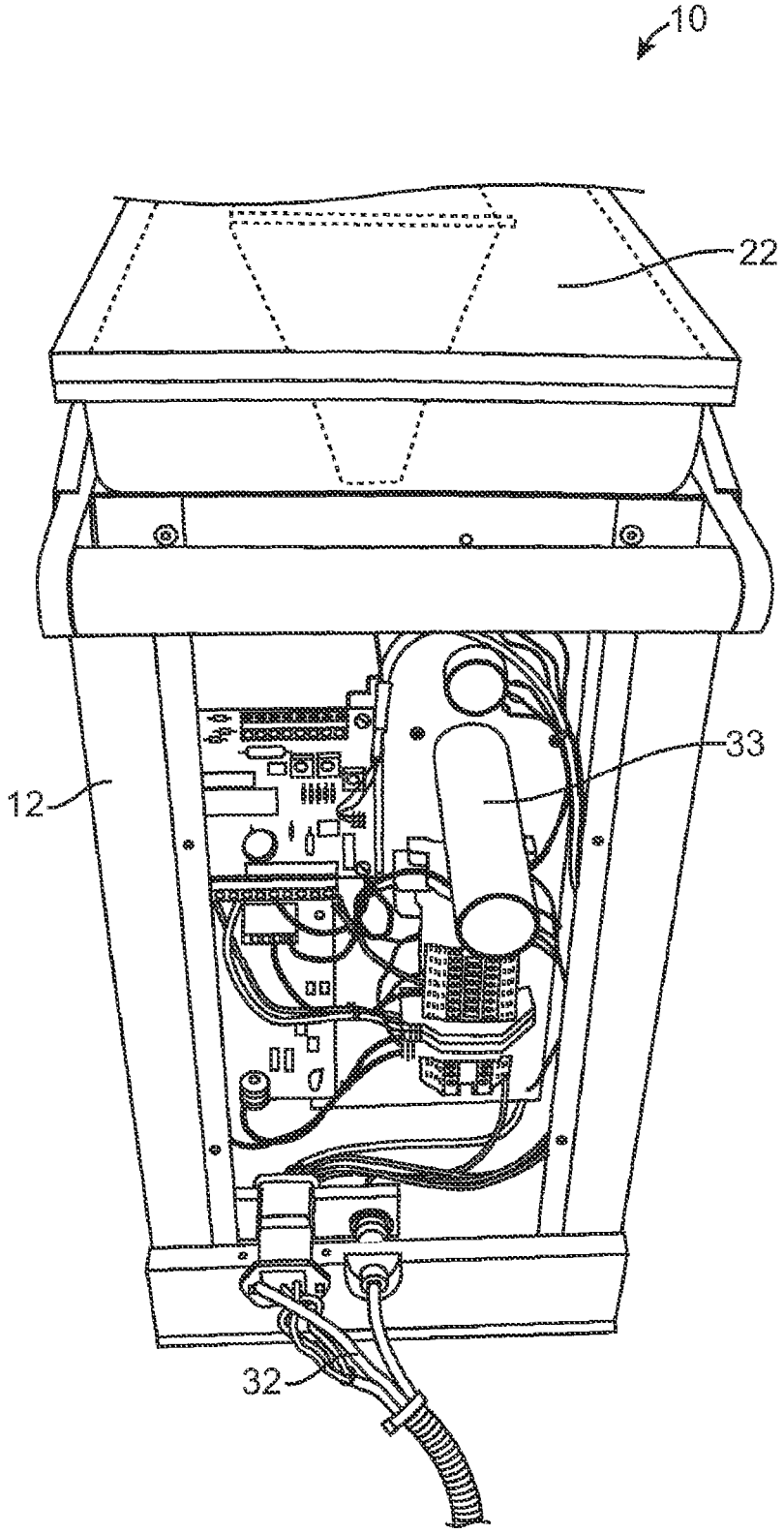
FIG. 4 is a rear perspective view of a pill dispensing device according to an embodiment.

Now referring to FIG. 4, a rear perspective view of a pill dispensing device 10 is illustrated. Again, a panel is removed from the frame 12 to better see the elements and components inside. Power, network, and pneumatic lines 32 extend into the pill dispensing device. The power, network, and pneumatic lines 32 serve the various electronic controls and circuit boards adapted to facilitate the operation of the pill dispensing device 10. A top portion of the hopper 22 is also illustrated from this rear perspective view.

Additionally, an elongated tube 33 is shown. The rear panel (not shown) includes a bore through which an end of the elongated tube 33 extends. The elongated tube 33 interfaces with the filtration assembly of the pill dispensing device 10. The filtration assembly is adapted to remove air, dust, and particulate matter from an interior cavity of the housing. In some embodiments, the filtration system provides a negative air pressure situation (or close to a negative air pressure system) within the interior of the device. The elongated tube 33 acts to suck or remove air, as well as dust and particulate matter, out of the interior of the pill dispensing device 10.

Figure 5:
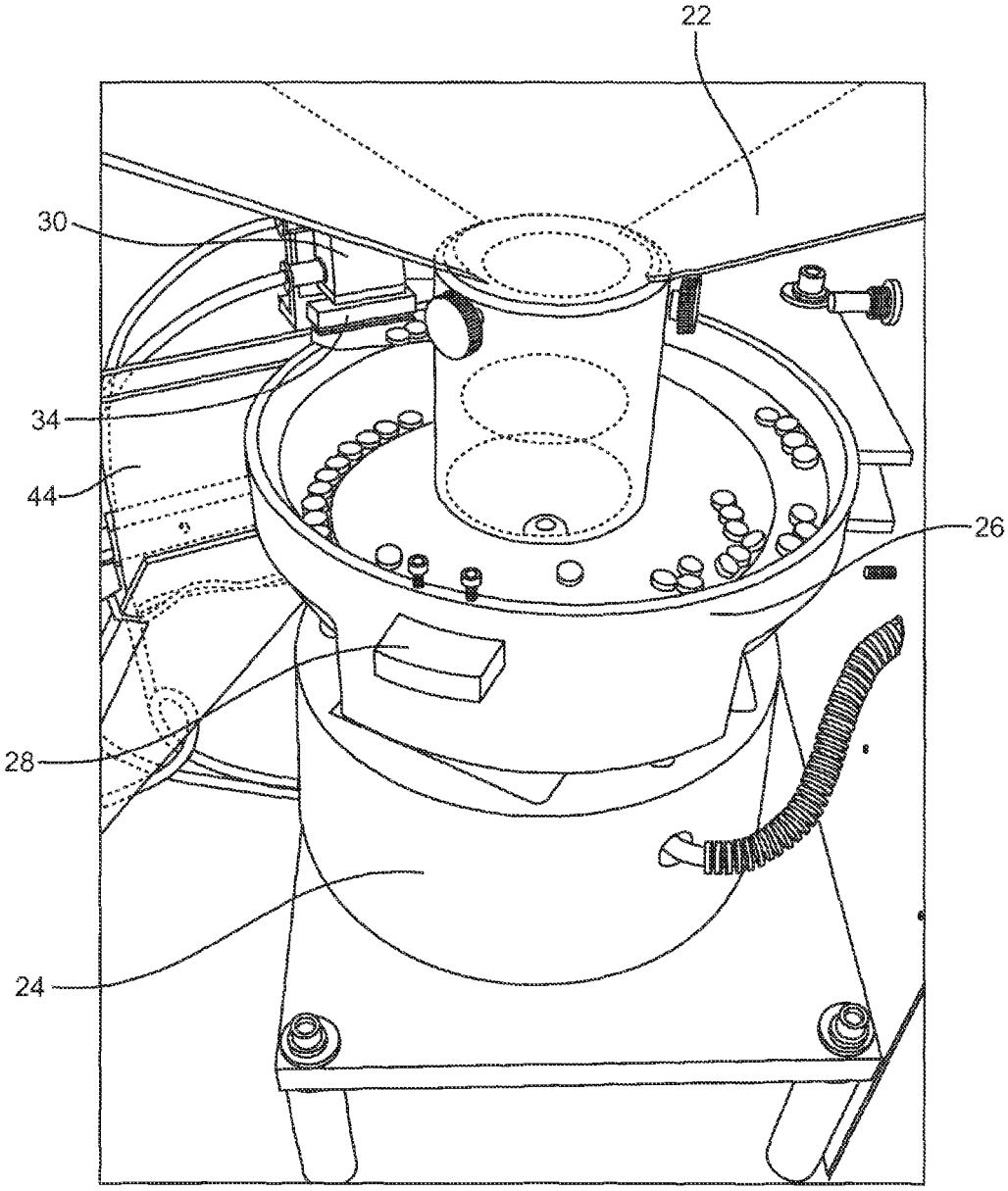
FIG. 5 is a close-up perspective view of a feeding assembly of a pill dispensing device according to an embodiment.

FIG. 5 is a close-up perspective view of the feeding assembly of the pill dispensing device 10 according to an embodiment. The vibratory base unit 24, the vibratory feeder bowl 26, and the singulator 28 are shown while operation. Pills are shown aligning along the spiraling edge of the vibratory feeder bowl 26. Additionally, a brake shoe 34 of the pneumatic pill stopping mechanism 30 can be seen. The brake shoe 34 and the entire pneumatic pill stopping mechanism 30 are located proximate the exit edge of the vibratory feeder bowl 26 and the upper portion 44 of the dispensing route. Pneumatic lines connected to the pneumatic pill stopping mechanism 30 are illustrated as well.

Figure 6:
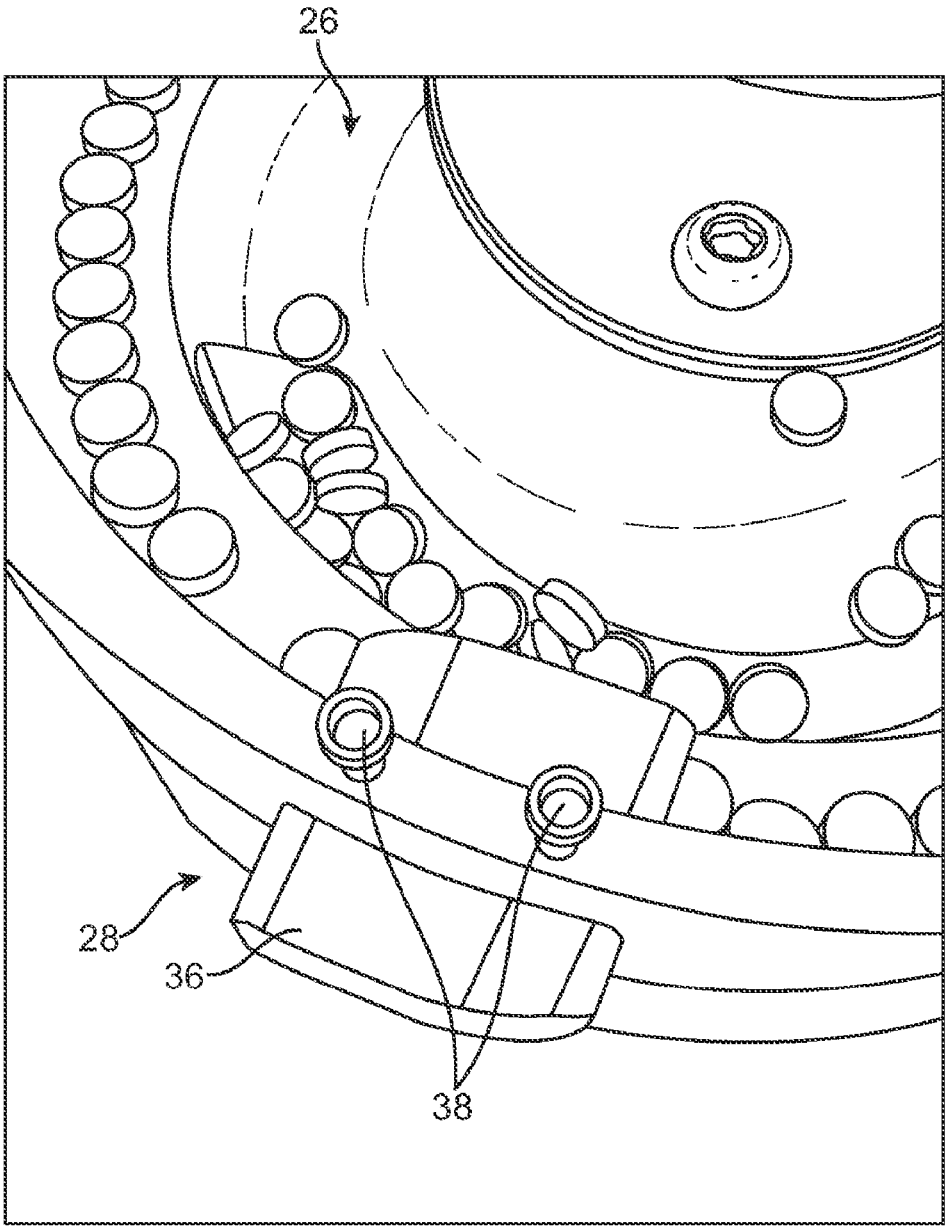
FIG. 6 is a close-up top perspective view of a singulator of a pill dispensing device according to an embodiment.

FIG. 6 is a close-up top perspective view of the singulator 28 of the pill dispensing device 10. In an embodiment, the singulator 28 comprises a beveled piece 36 that extends through a side wall of the vibratory feeder bowl 26. The beveled piece 36 typically, but not necessarily, is made of plastic material and looks similar to a small wedge. A bottom surface of the beveled piece 36 (not shown from this top perspective) faces the spiraling edge of the vibratory feeder bowl 26. The bottom surface is essentially an inside edge of the beveled piece 36 that beveled over the spiraling edge (or ledge) of the vibratory feeder bowl 26. The bevel of the inside edge increases (or essentially becomes narrower) proximal the center of the vibratory bowl 26. A top portion of the beveled piece 36 is relatively flat.

Accordingly, as pills a pass on under the beveled piece 36 any pills stacked wholly or partially on top of one another are separated. During this operation, the beveled piece 36 typically causes some pills to fall over the ledge or spiraling edge back into the vibratory bowl 26. After passing the singulator 28, the pills are situated or arranged in a generally side-by-side, single file line fashion along a remaining portion of the spiraling edge as they progress towards the exit edge of the vibratory feeder bowl 26. Since pills vary in size, two adjustment fasteners 38 (typically screws) comprise part of the singulator 28 in order to secure the beveled piece 36 in place once it is has been radially positioned relative to the vibratory feeder bowl 26 for pills of a particular size.

Figure 7:
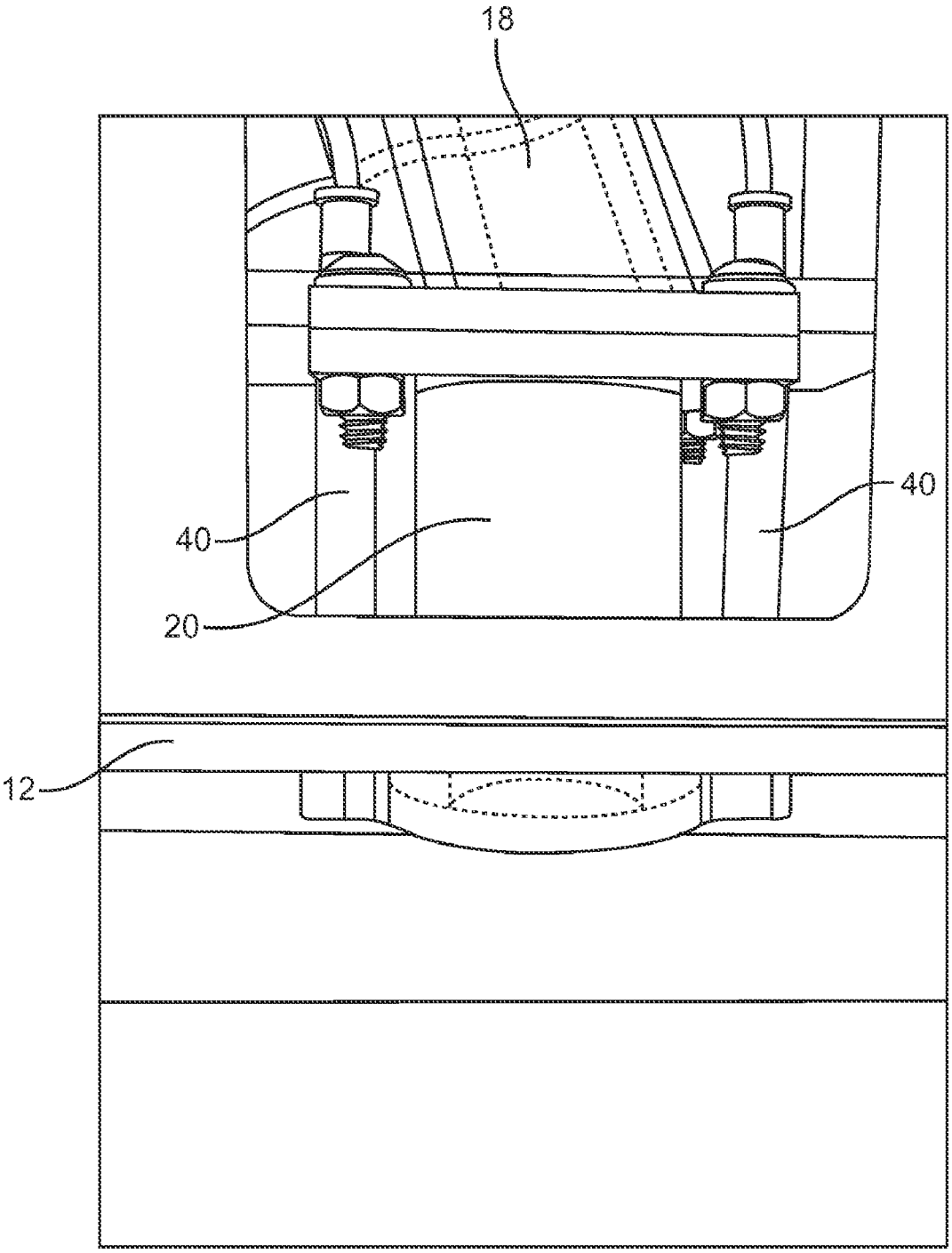
FIG. 7 is a close-up front perspective view of a dispensing neck of a pill dispensing device according to an embodiment.

Now referring to FIG. 7, a close-up front perspective view of the dispensing neck 20 of the pill dispensing device 10 is illustrated. As previously described, the dispensing route of the embodiments of the pill dispensing device 10 can vary significantly. Essentially, the dispensing route is generally a line or path of travel for the pills as they leave or drop from the exit position of the feeding assembly. In some embodiments, the dispensing route need not include any (or very few) structural elements as the pills may drop straight down from the feeding assembly passing the plurality of optical sensors and out a dispensing end of the dispensing route. However, the dispensing route more typically comprises one or more chute portions and a neck to direct the movement of the pills as they move through embodiments.

The dispensing end of the pill dispensing device 10 is a dispensing neck 20. The dispensing neck 20 is coupled to the lower portion of the dispensing chute 18 and moveably coupled proximate a bottom end of the frame 12. As illustrated in FIG. 7, the dispensing neck 20 along with its associated assembly in the retracted position. The dispensing neck 20 is typically but not necessary in the retracted position when the pill dispensing device 10 is not actively dispensing pills. One or more pneumatic actuators 40 can be coupled to the dispensing neck 20 to facilitate the movement thereof. Of course, in other variations one or more solenoids and/or other mechanisms can be used in place of the pneumatic actuators.

Figure 8:
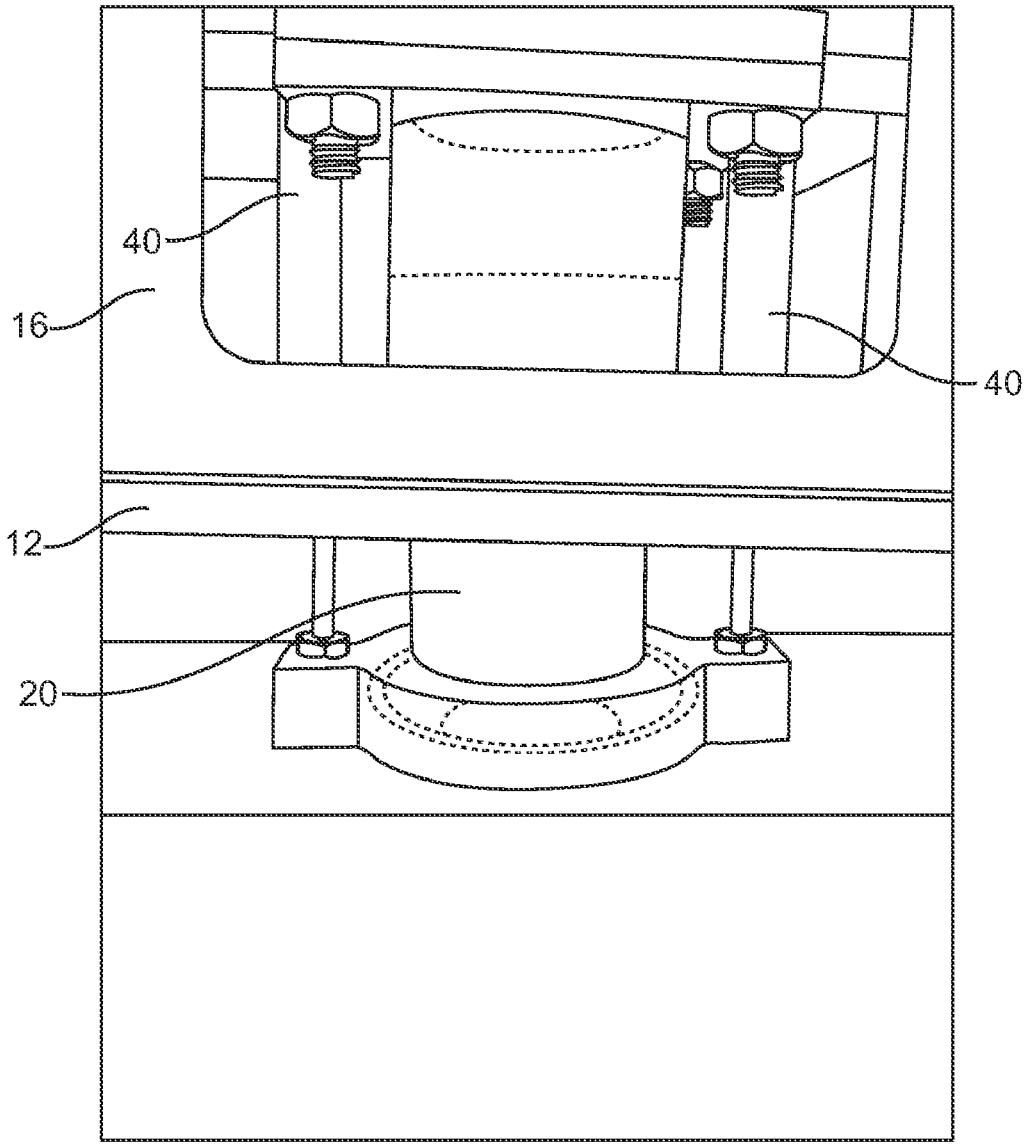
FIG. 8 is a close-up front perspective view of a dispensing neck in an extended configuration according to an embodiment.

Now referring to FIG. 8, the dispensing neck 20 can be seen in the extended position. A portion of the dispensing neck 20 can be seen through the window of the front door panel 16 and a portion can be seen downwardly extended beyond the bottom end of the frame 12. The extended position can be achieved upon activation the two pneumatic actuators 40. Typically the dispensing neck 20 is in the extended position when the pill dispensing device 10 is actively dispensing pills.

Figure 9:
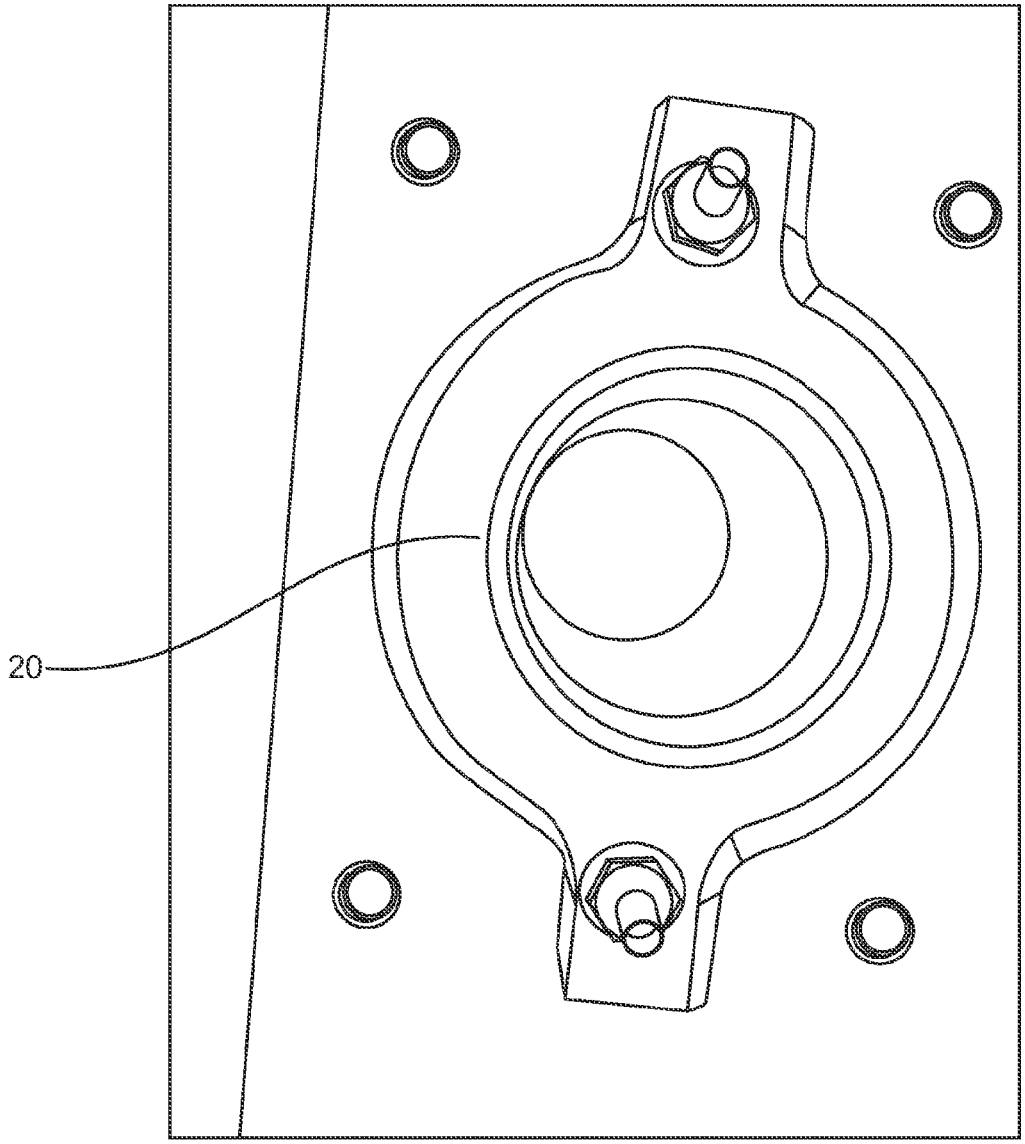
FIG. 9 is a close-up bottom perspective view of a dispensing neck according to an embodiment.
Figure 10:
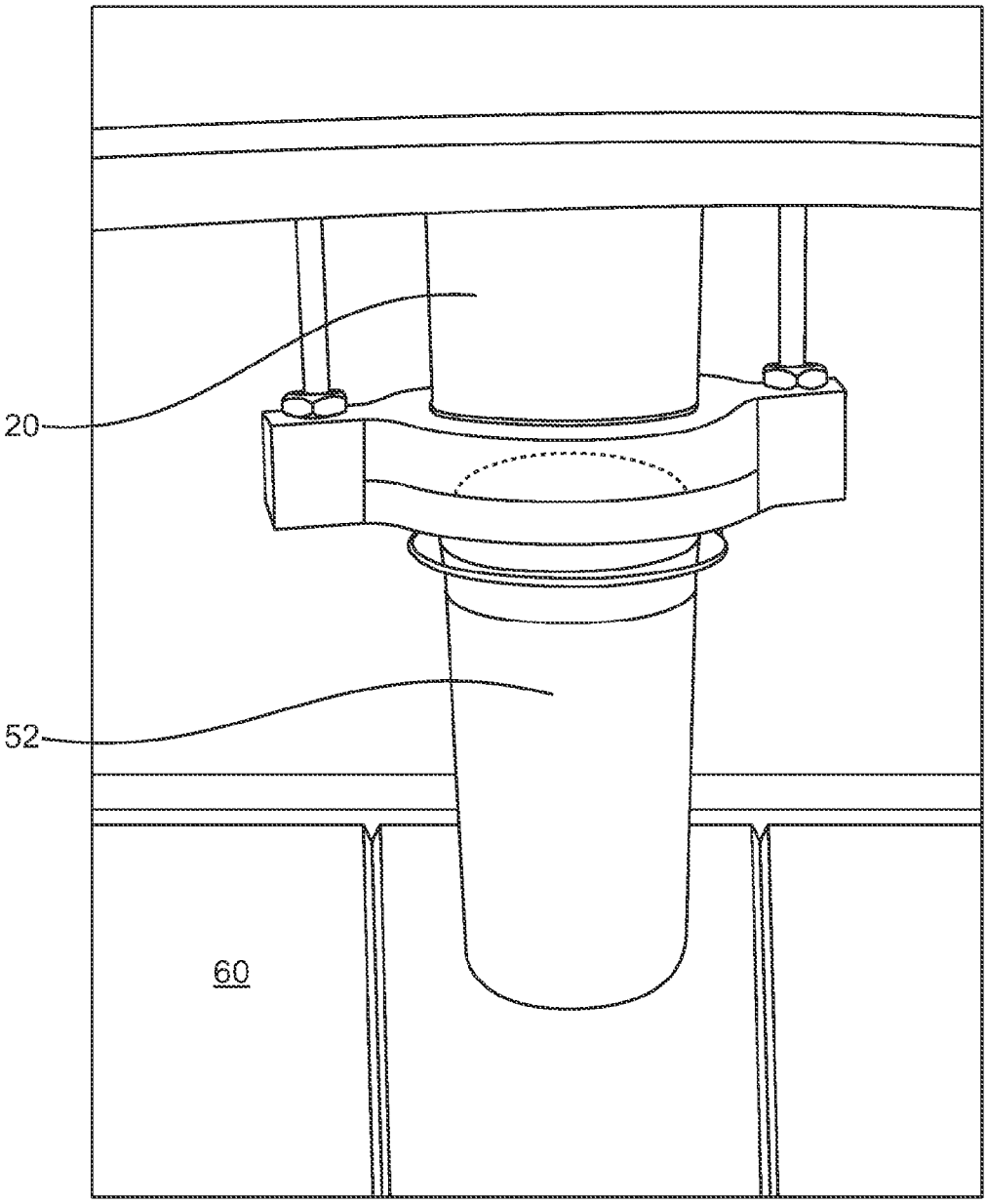
FIG. 10 is a close-up front perspective view of a pill bottle engaged with a dispensing neck in an extended configuration according to an embodiment.

FIG. 9 is a close-up bottom perspective view of the dispensing neck 20. As illustrated, the dispensing neck 20 comprises a circumferential channel extending around a neck opening. The circumferential channel is adapted to fit around an annular top edge of a pill bottle. Thus, the dispensing neck 20 can be generally sealed or pressed to the pill bottle in order to prevent pills from falling outside of the pill bottle. Now referring to FIG. 10, a close-up front perspective view of a pill bottle 52 engaged with the dispensing neck 20 is illustrated. The dispensing neck 20 is the extended configuration while engaged with the pill bottle 52. The pill bottle may be on a conveyor belt 60 as illustrated or other similar apparatus or system adapted to route the pill bottle to the pill dispensing device 10.

Moreover, the dispensing neck 20 can be automatically extended and retracted by the controller. It is advantageous to have the pill dispensing neck 20 be extendable and retractable when the pill dispensing device 10 is used in combination with a conveyor belt system and/or a plurality of pill dispensing devices. Hence, pill bottles can pass by one pill dispensing device 10 en route to another pill dispensing device without contacting the pill dispensing neck 20 and knocking the pill bottles over or otherwise altering their position on the conveyor belt 60.

Figure 11:
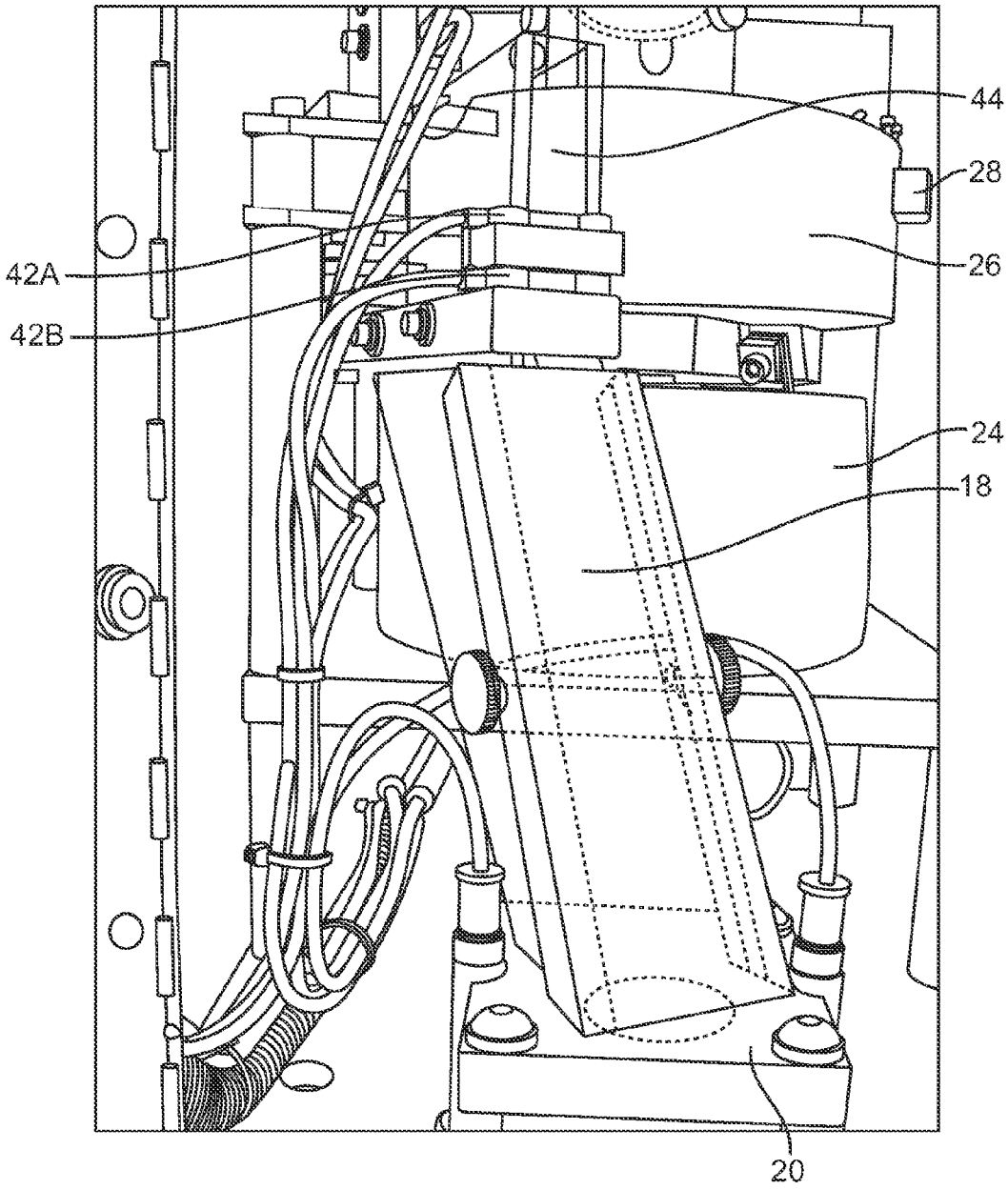
FIG. 11 is a close-up front perspective view of a dispensing chute according to an embodiment.

FIG. 11 is a close-up front perspective view of the dispensing chute 18 and its coupling to the dispensing neck 20. The dispensing chute 18 can be seen relative to the vibratory base 24 and the vibratory feeder bowl 26. The dispensing route of pill dispensing device 10 typically comprises the upper portion 44 proximate and operatively coupled to the exit position of the feeding assembly. The upper portion 44 generally comprised the light beam (when active) of each optical sensor therein. Two sensor heads 42a and 42b are adjacent the upper portion 44 of the dispensing route. As can be depicted by the angle of the dispensing chute 18, at least a portion of the dispensing chute 18 is configured to change the direction of the pills moving down the dispensing chute 18 and into the dispensing neck 20.

Figure 12:
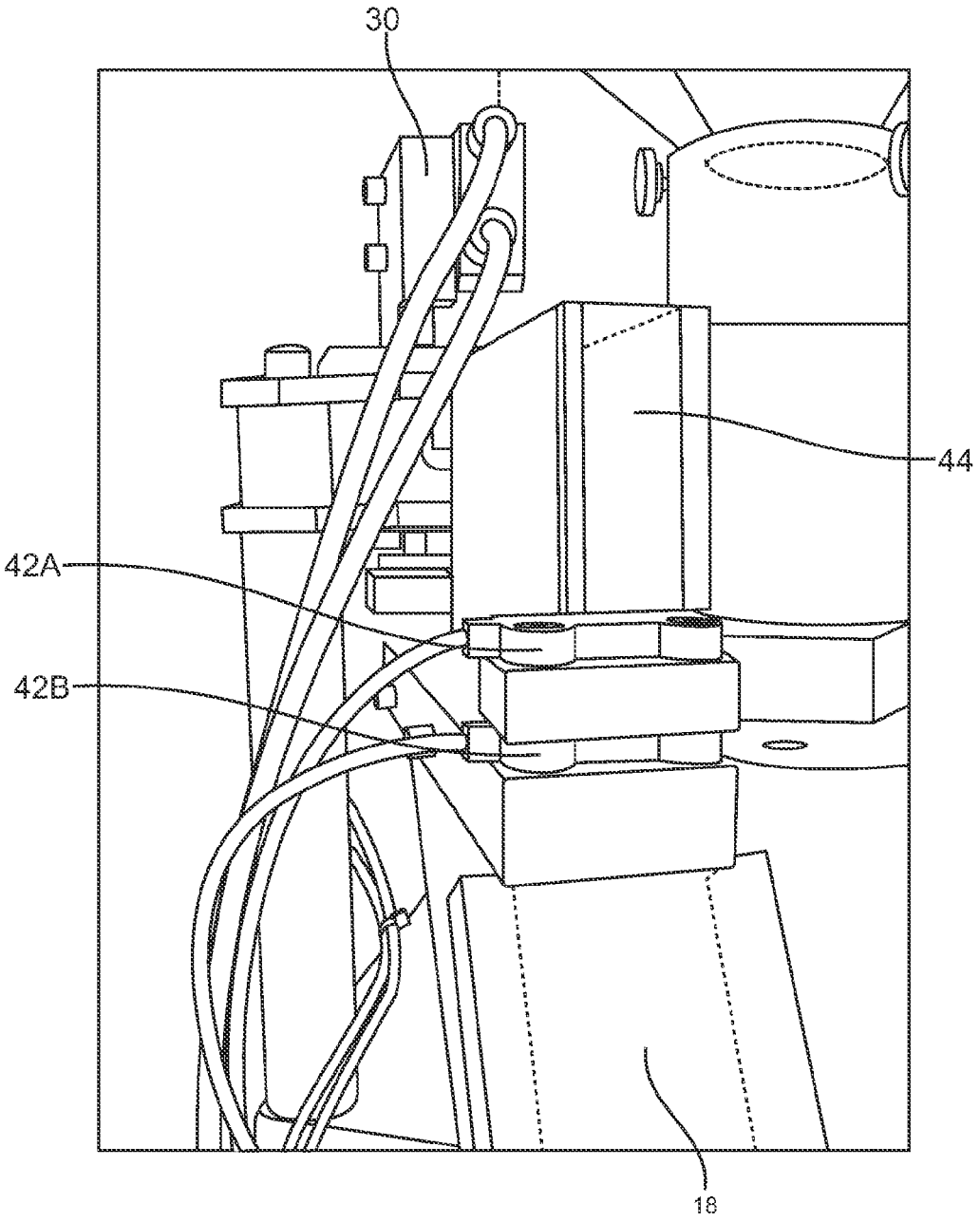
FIG. 12 is a close-up front perspective view of an upper portion of a dispensing chute and optical sensor heads according to an embodiment.
Figure 13:
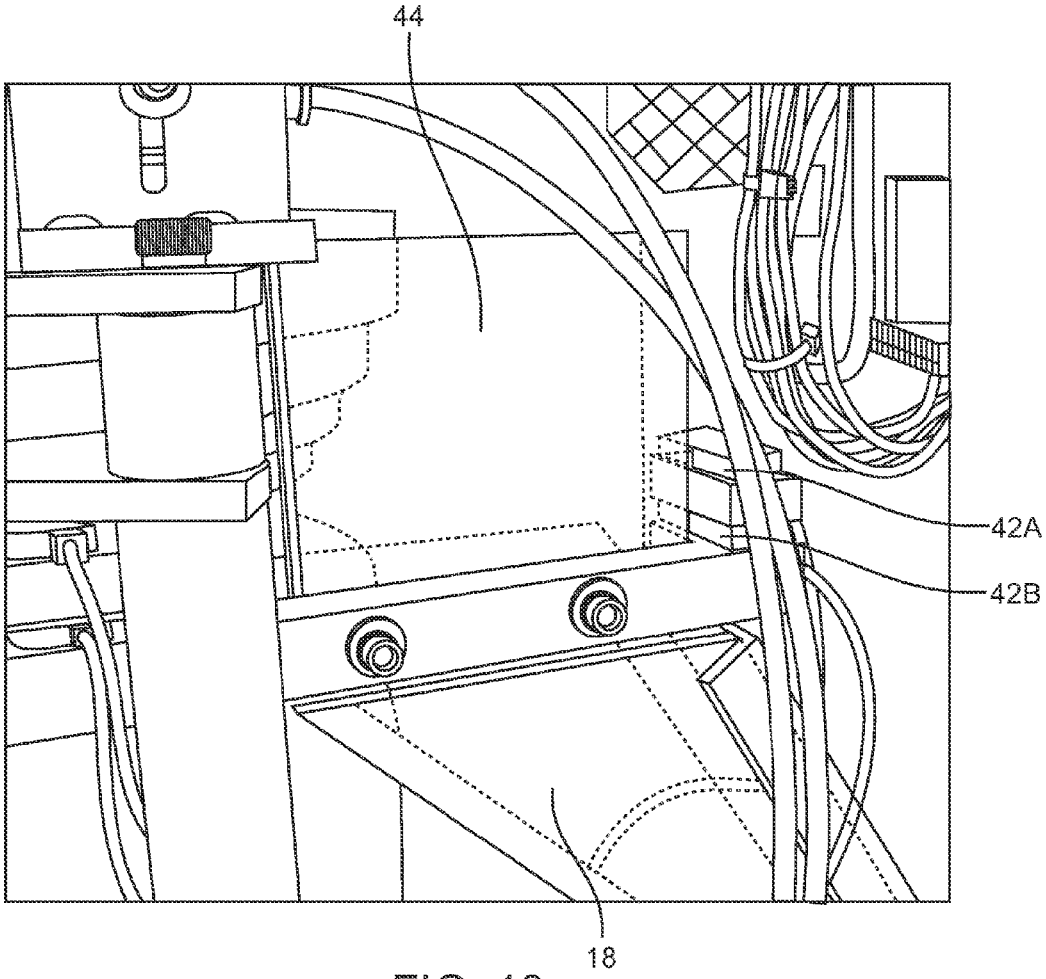
FIG. 13 is a close-up side perspective view of an upper portion of a dispensing chute and optical sensor heads according to an embodiment.

Now referring to FIG. 12, the upper portion 44 and two sensor heads 42a and 42b can be seen from a different perspective. An interior cavity of the upper portion 44 where the pills fall through can be seen from this perspective. Additionally, the upper portion 44 can be seen with respect to the pneumatic pill stopping mechanism 30. FIG. 13 illustrates a close-up side perspective view of the upper portion 44. The orientation of sensor heads 42a and 42b can be better pbserved from this perspective. Moreover, the coupling between the upper portion 44 and the dispensing chure 18 is illustrated.

Figure 14:
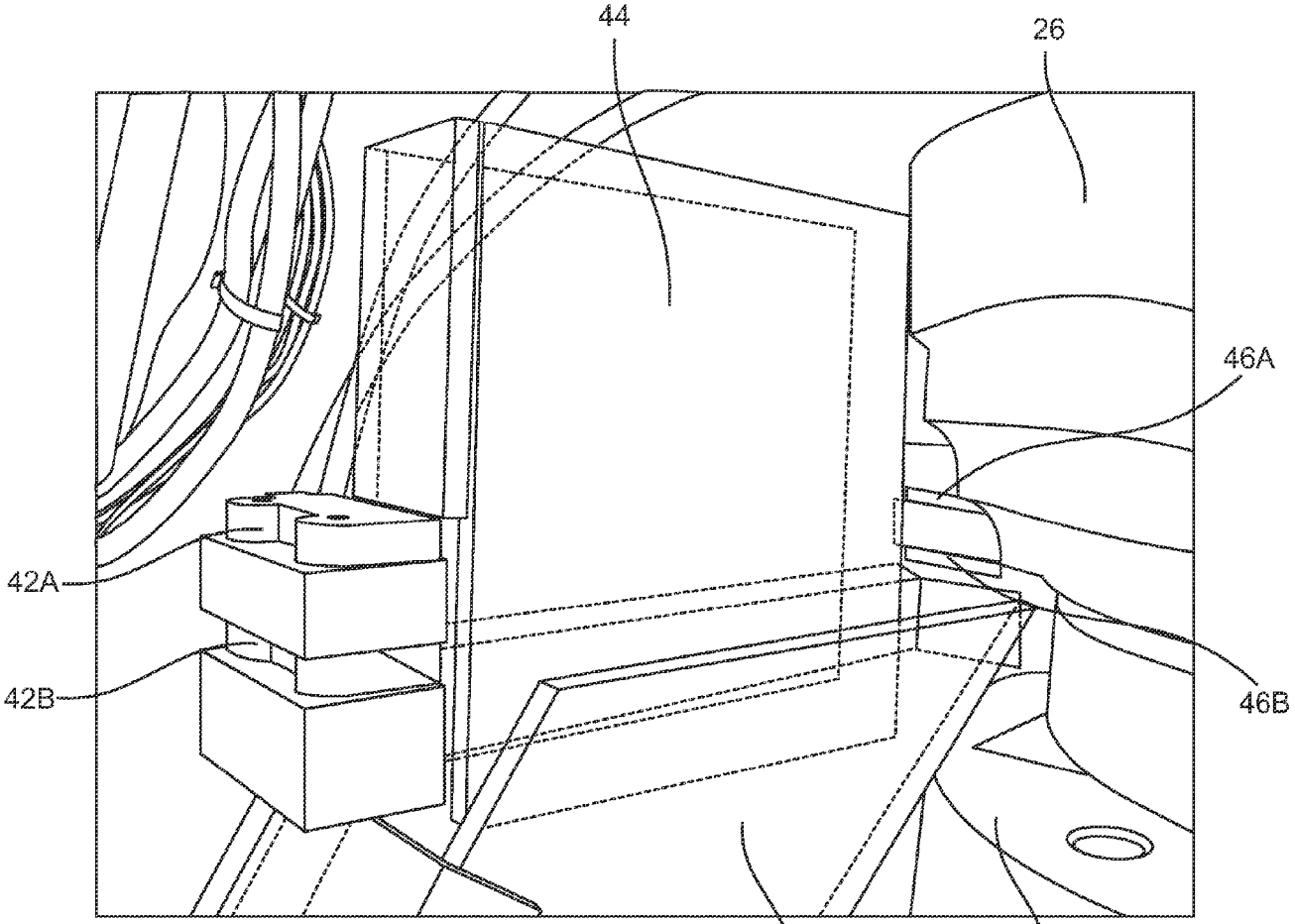
FIG. 14 is a close-up front and side perspective view of an upper portion of a dispensing chute and optical sensor heads according to an embodiment.

FIG. 14 shows the upper portion 44 of the dispensing route and the dispensing chute 18 with a plurality of optical sensor heads. Sensor head 42a operates in conjunction with sensor head 46a located proximal the vibratory feeder bowl 26. Similarly, sensor head 42b operates in conjunction with sensor head 46b. In one embodiment, a first pair of sensor heads 42a & 46a and a second pair of sensor heads 42b & 46b are capable of operating in a plurality of configurations. For example, one of the sensor heads either 42a or 46a of the first pair can be a light projecting sensor head and the other can be a light receiving sensor head. Likewise, one of the sensor heads either 42b or 46b of the second pair can be the light projecting sensor head and the other can be the light receiving sensor head.

In operation, pills fall off the exit edge of the vibratory feeder bowl 26 into the upper portion 44. As the pills fall through the upper portion 44, the pills pass in front of each sensor pair and then into the dispensing chute 18. The pills then pass through the dispensing chute 18 and eventually exit the pill dispensing device 10 through the pill dispensing neck 20 and into the pill bottle.

Figure 15:
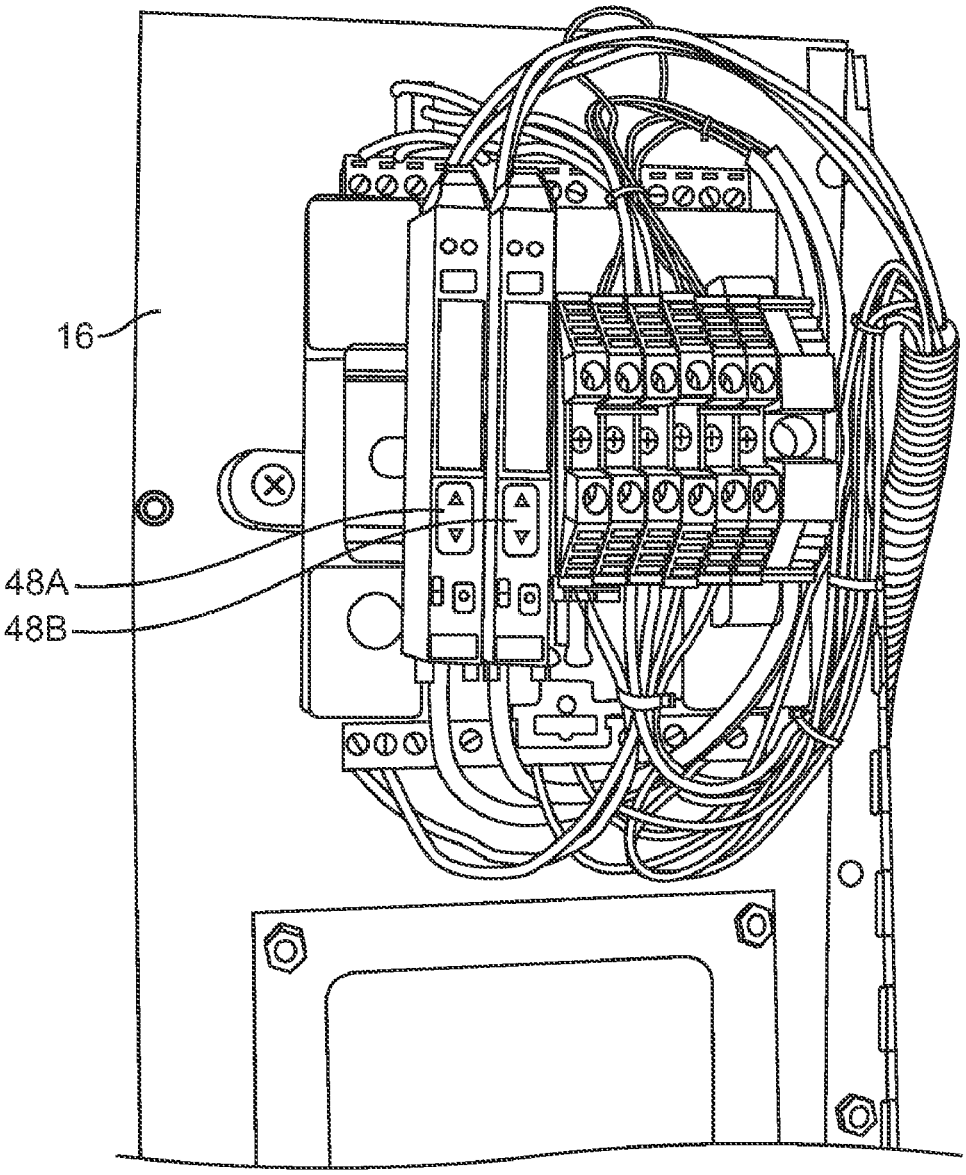
FIG. 15 is a close-up front perspective view of a controller of a pill dispensing device according to an embodiment.

FIG. 15 is an illustration of the controller of the pill dispensing device 10 according to an embodiment. The controller can be mounted to an inside surface of the front door panel 16. The controller may comprise a typical programmable logic controller (PLC) or similar programmable controller. The controller includes a processor such as a conventional microprocessor, typical computer system processor (see FIG. 24 and discussion thereof), or a digital signal processor. The controller and processor therein may also comprise static and/or dynamic memory and other associated circuitry and devices adapted to store data and instructions for the processor. The controller of the pill dispensing device 10 is operatively coupled to communicate with various elements and components of the pill dispensing device 10, and in particular the plurality of optical sensors.

For each optical sensor included in the pill dispensing device 10, there will typically be an associated optical sensor controller. The optical sensor controller provides a variety of functions and comprises a variety of components associated with the operation of the optical sensor. The optical sensor controller typically includes a light emitting component and a light detecting component. The light emitting component typically includes a laser diode or a light emitting diode;

however, other light and other electromagnetic wave projecting components are contemplated. The light detecting component of the optical sensor controller typically includes some amplification of the detected signal.

Figure 16:
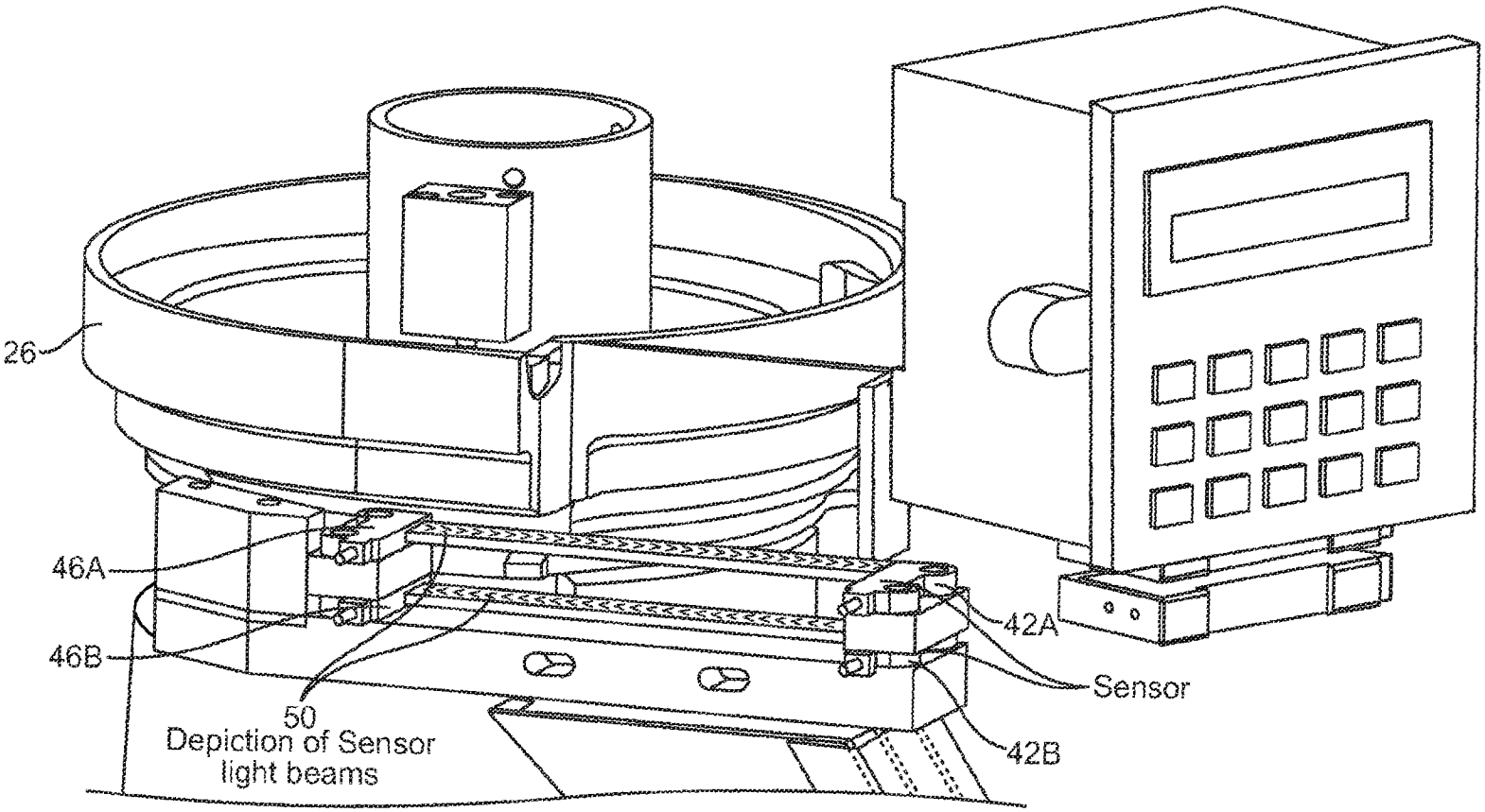
FIG. 16 is a close-up side perspective view of optical sensor heads and light beams thereof according to an embodiment.

Two optical sensor controllers 48a and 48b are shown operatively coupled and attached to the controller in FIG. 15. With reference to FIG. 16, a first optical sensor controller 48a is operatively coupled (typically optically via a fiber optic cable) to the first pair of sensor heads 42a & 46a. Similarly, a second optical sensor controller 48b is operatively coupled (typically optically via a fiber optic cable) to the second pair of sensor heads 42b & 46b. Top sensor head 42a interfaces and is aligned with its opposing top sensor 46a while bottom sensor 42b interfaces and is aligned with its opposing your bottom sensor 46b. Each sensor head typically comprises a lens and or other means to direct rays of light. A light beam 50 is created between each pair of sensor heads. For example, a first light beam 50 is created between the first pair of sensor heads 42a & 46a as activated and controlled by the first optical sensor controller 48a. Similarly, a second light beam 50 is created between the second pair of sensor heads 42b & 46b as activated and controlled by the second optical sensor controller 48b. In some embodiments, the two optical sensor controllers 48a and 48b operate in a master/slave relationship whereby only one of the two pairs of sensor head (either the first pair of sensor heads 42a & 46a—or—the second pair of sensor heads 42b & 46b) are projecting a light beam or essentially a pulse of a light beam at any instance in time.

In use, when a pill drops between the sensor pair, a disruption to the light beam is recorded by the optical sensor controller a count. Moreover, the disruption need not and typically is not be a complete blockage of the light beam, but rather the detection of a change in intensity of the light beam. The first and second sensor pairs operate in a substantially identical manner. Each sensor pair independently counts the number of times a pill (or any other object being counted) passes through its respective light beam. Preferably, the optical sensors and the sensor pairs thereof comprise fiber-sensing type technologies although any suitable type of optical sensor may be utilized in variations. Furthermore, while only two sensor pairs are illustrated in the various figures, it is to be appreciated that pill dispensing devices having additional optical sensors and the sensor pairs thereof have been disclosed and are contemplated to further improve count accuracy.

It is also pertinent to note that in some embodiments, the controller of each pill dispensing device 10 in turn transmits count information to a centralized computer system or other type of centralized controlling unit. The centralized computer system typically monitors and controls the operation of an entire facility of pill dispensing devices.

Still referring to FIG. 16, the light beam can be seen relative to the exit edge of the vibratory feeding bowl 26. As illustrated the first pair of sensor heads 42a & 46a is typically, but not necessarily, generally latitudinally aligned with the other. Similarly, the second pair of sensor heads 42b & 46b is typically, but not necessarily, generally latitudinally aligned with the other. Moreover, a first plane of the first light beam 50 is generally perpendicular with respect to the dispensing route or at least a portion thereof and a second plane of the second light beam 50 is generally perpendicular with respect to the to the dispensing route or at least a portion thereof. As can be seen, the first plane is proximal and the second plane is distal the exit edge of the vibratory feeder bowl 26 along a generally longitudinal axis of the upper portion of dispensing route (i.e., a longitudinal axis or path similar to that of a pill drop straight down the inner cavity of the upper portion of the dispensing route).

Figure 17:
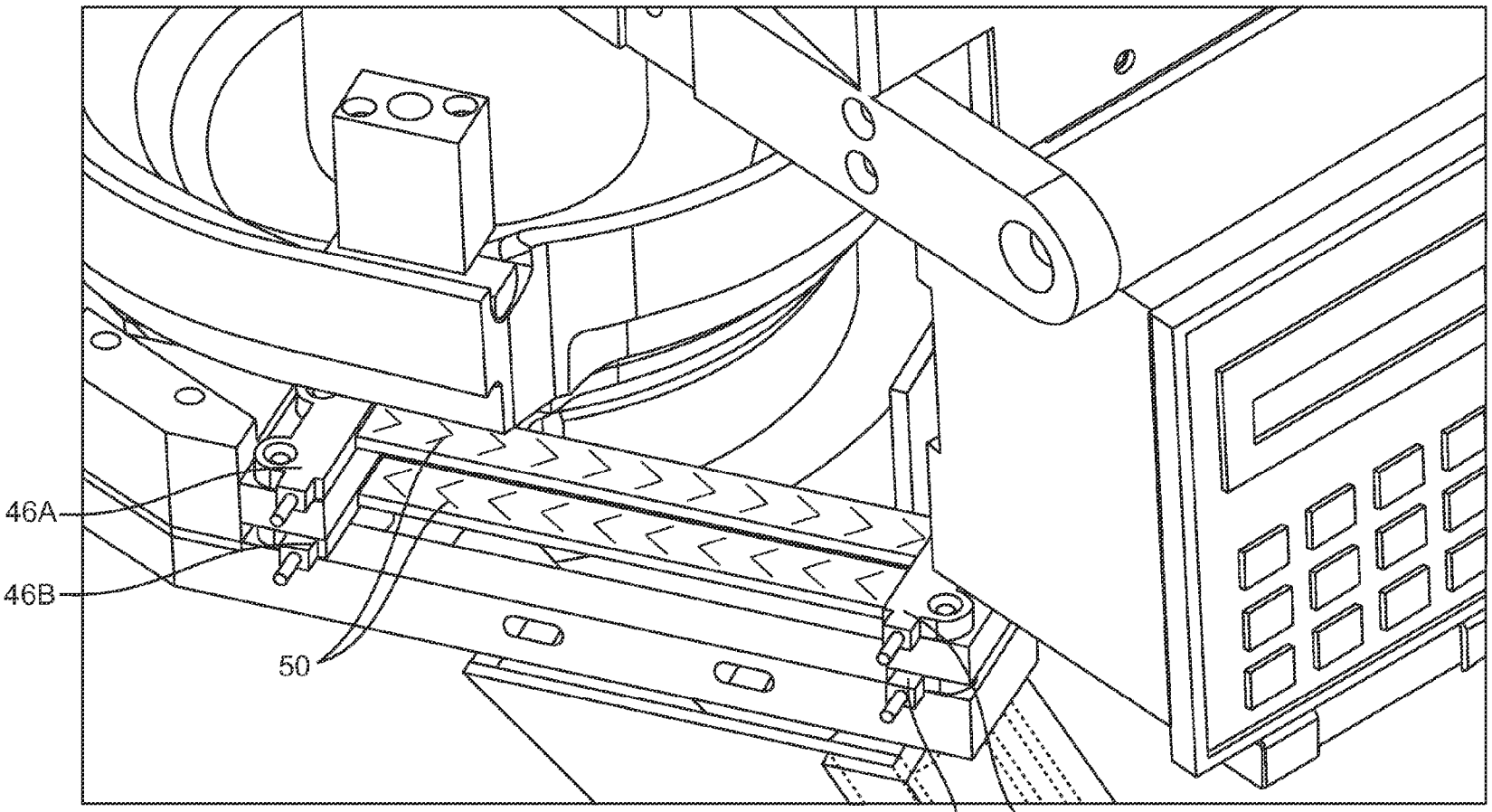
FIG. 17 is a close-up top perspective view of optical sensor heads and light beams thereof according to an embodiment.
Figure 18:
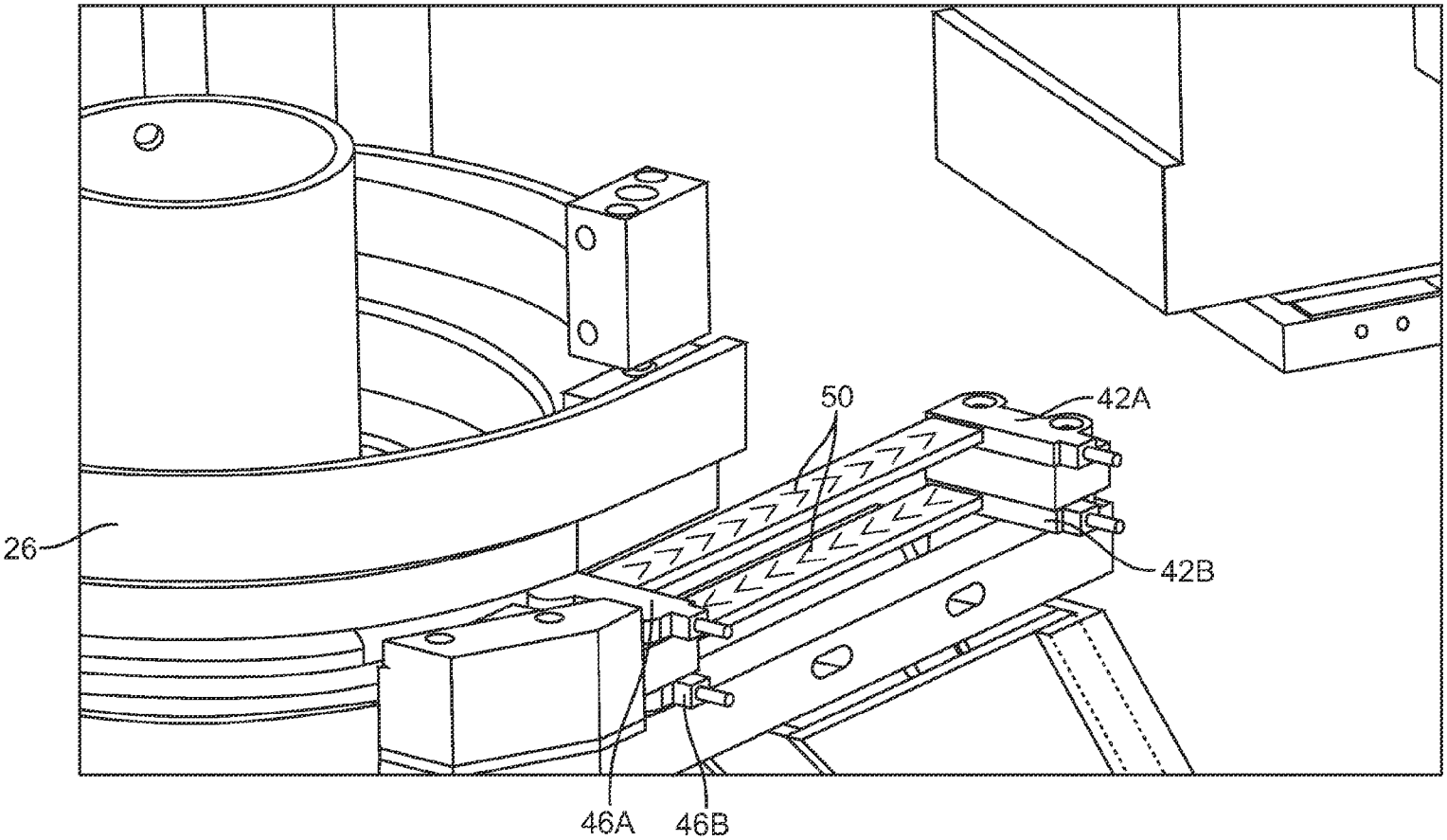
FIG. 18 is a close-up top and side perspective view of optical sensor heads and light beams thereof according to an embodiment.

FIGS. 17 and 18 illustrate close-up perspective views of the first pair of sensor heads 42a & 46a and the second pair of sensor heads 42b & 46b with their corresponding light beams 50. In one variation of the pill dispensing device 10, a first distance from the exit edge of the vibratory feeder bowl 26 to the first light beam 50 of the first pair of sensor heads 42a & 46a is approximately between 1 inch and 2 inches. Additionally, a second distance from the first light beam 50 of the first pair of sensor heads 42a & 46a to the second light beam 50 of the second pair of sensor heads 42b & 46b is approximately between 0.25 inch and 0.75 inch.

Figure 19:
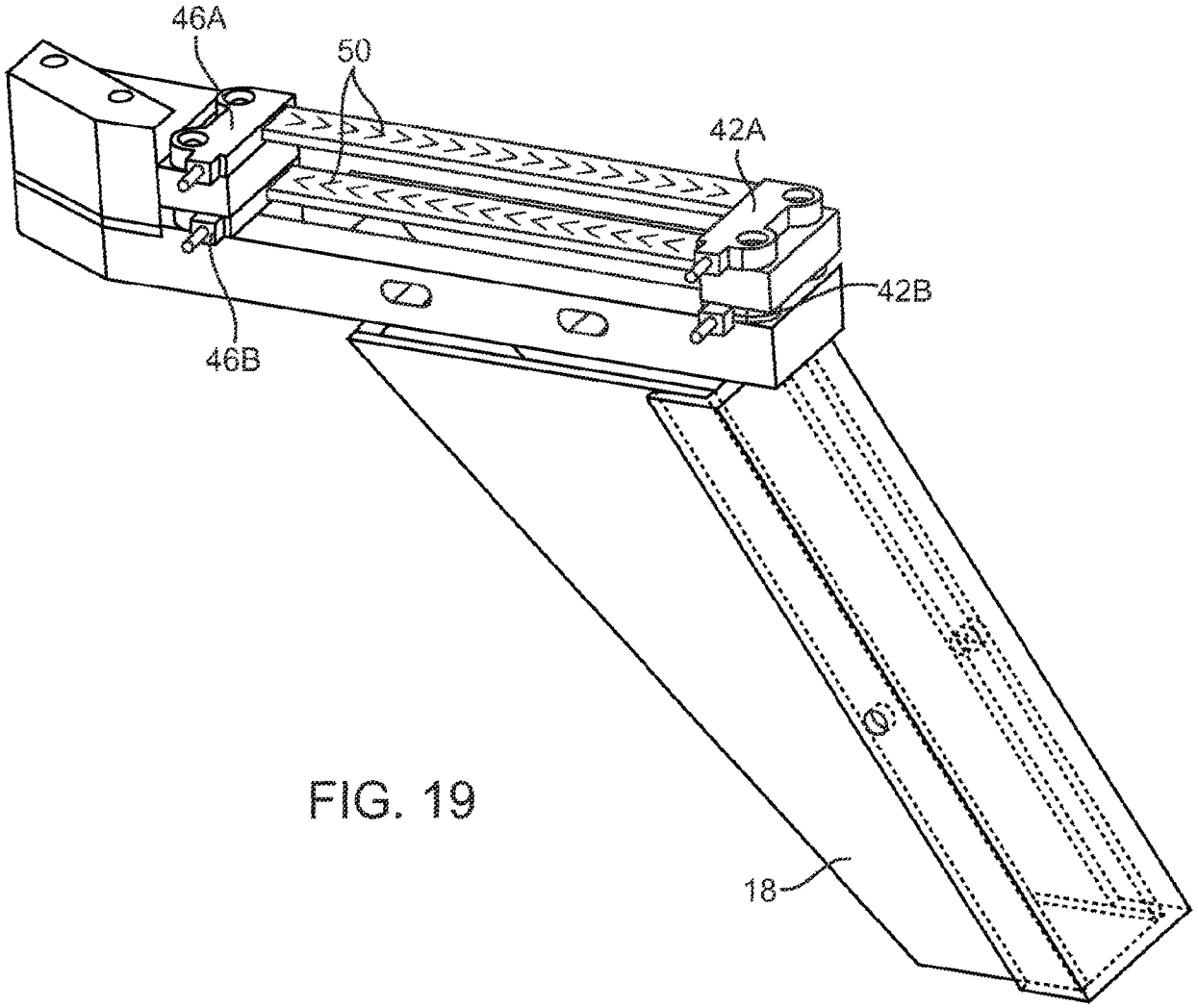
FIG. 19 is an exploded side perspective view of optical sensor heads and light beams thereof and a dispensing chute according to an embodiment.

FIG. 19 is an exploded perspective view of the first pair of sensor heads 42a & 46a and the second pair of sensor heads 42b & 46b with their corresponding light beams 50. The relationship of the light beams 50 and the optical sensor heads with respect to the dispensing chute 18 is illustrated from this perspective view. Also of note is that in one embodiment of the pill dispensing device 10 a distance between the first sensor head 42a and first sensor head 46a is approximately between 4 inches and 6 inches. Similarly, a distance between the second sensor head 42b and second sensor head 46b is also approximately between 4 inches and 6 inches.

Figure 20:
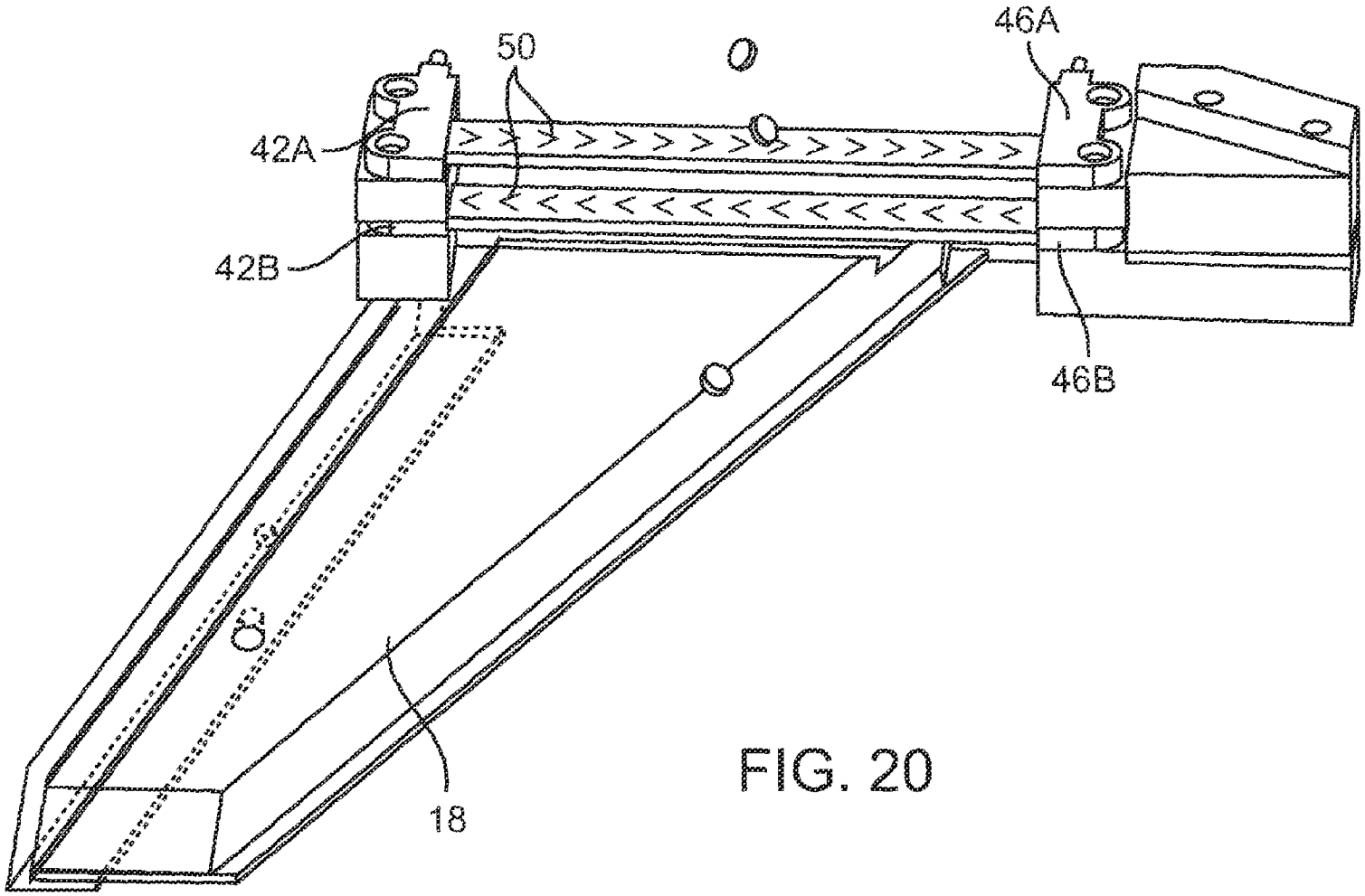
FIG. 20 is an exploded side and top perspective view depicting pills falling through light beams and into a dispensing chute according to an embodiment.

Referring now to FIG. 20, a perspective view depicting pills falling through light beams 50 of the first pair of sensor heads 42a & 46a and the second pair of sensor heads 42b & 46b is illustrated. The pills can also be seen falling down into the dispensing chute 18. As each pill passes through a light beam 50, a count is made and recorded. Ideally, the count determined by each sensor pair for particular dispensing operation should be identical.

In one embodiment, at least one light beam of the plurality of the optical sensors is projected in a substantially opposite direction than another light beam. As previously discussed, one of the sensor heads either 42a or 46a of the first pair can be the light projecting sensor head and the other can be the light receiving sensor head. For example, sensor head 42a can be the light projecting sensor head and sensor head 46a can be the light receiving sensor head (as depicted by the arrows in FIG. 20 and several other figures). However, sensor head 46b can be the light projecting sensor head and sensor head 42b can be the light receiving sensor head (as depicted by the arrows in FIG. 20 and several other figures). This configuration is advantageous in some embodiment to significantly reduce crosstalk that may be generated between the first and second sensor pairs that would typically manifest itself within the light emitting and light detecting components of their respective optical controllers.

Figure 21:
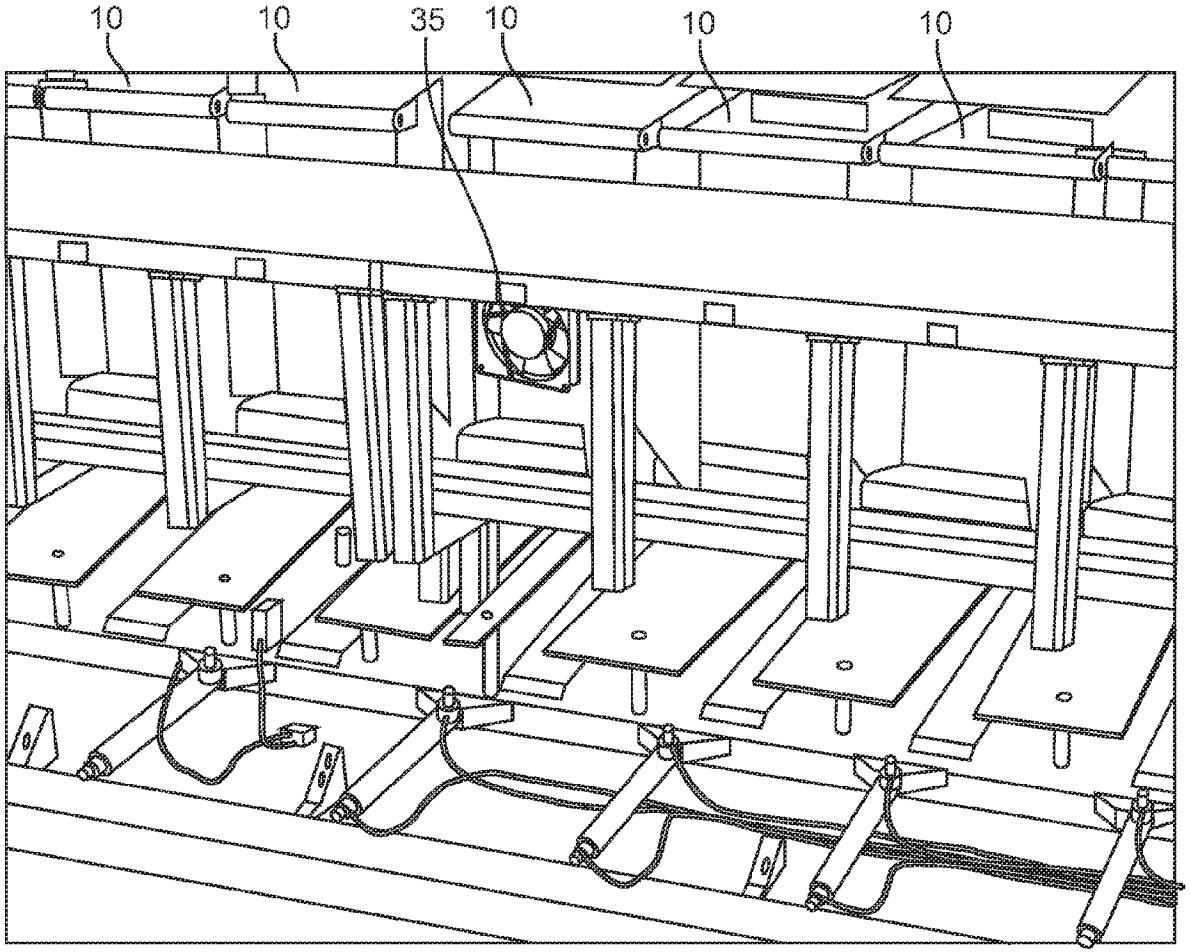
FIG. 21 is a rear perspective view of a bank of pill dispensing devices according to an embodiment.
Figure 22:
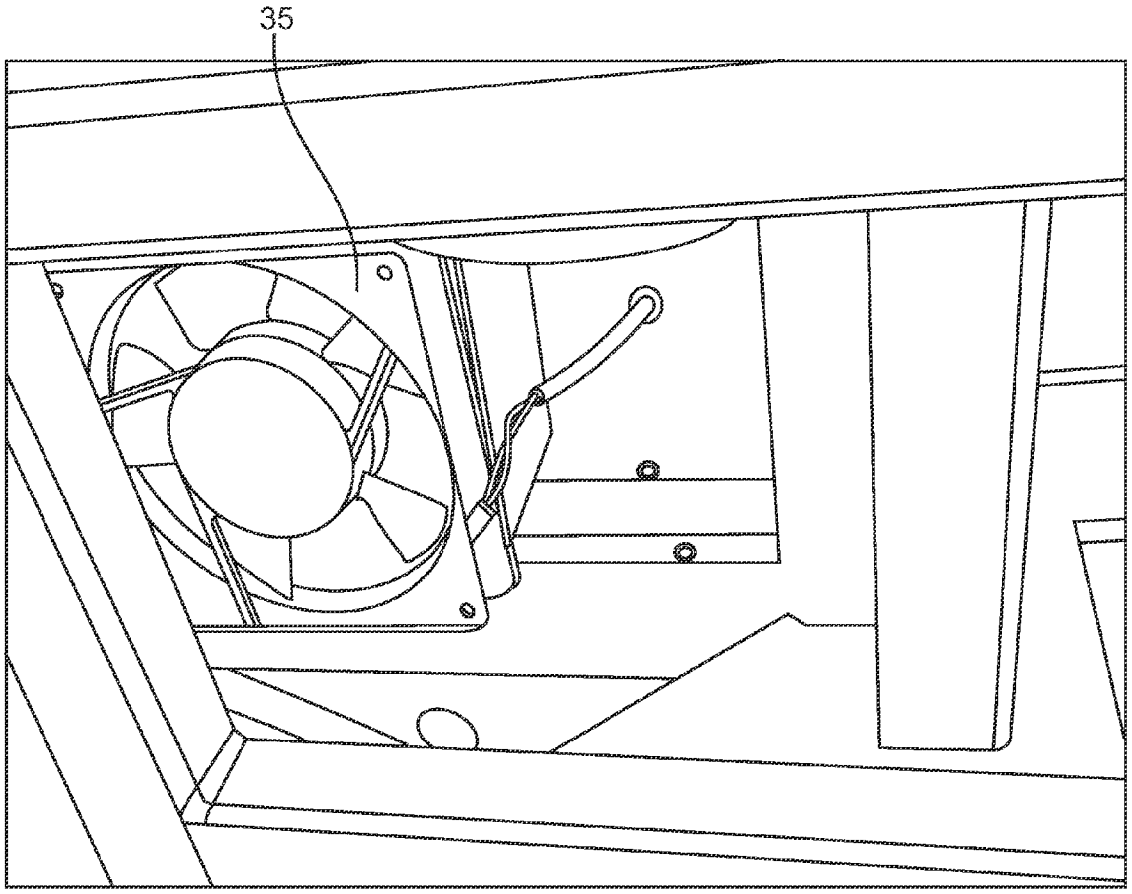
FIG. 22 is a close-up rear perspective view of a filtration assembly on a pill dispensing device in a bank of pill dispensing devices according to an embodiment.

FIG. 21 is a rear perspective view of a bank of pill dispensing devices 10 according to an embodiment. It is appreciated that in one installation, four banks of 50 devices can be utilized. Of particular note is that a center device includes a filtration system 35. The fan assembly of the filtration system 35 is coupled with the aforementioned tube 33 (see FIG. 4) and in operation acts to suck or remove air, dust, and/or particulate matter out of the interior of the pill dispensing device 10. In some embodiments, a negative pressure situation (or very nearly negative) is created within the interior of the housing of the pill dispensing device 10. This negative pressure situation can significantly aid in filtering the air that would otherwise be discharged back to the outside environment of the facility. A substantial portion of pill dust created during a dispensing operation is therefore captured in the filtration system 35. A closer view of the rear side of the pill dispensing device having the filtration assembly 35 is shown in FIG. 21. Moreover, it is to be appreciated that in one embodiment, the filtration system (HEPA, near HEPA grade, or otherwise) is only operational when pill dispensing activities are occurring and/or shortly thereafter. Additionally, the filtration assembly can be further adapted to transmit an alarm to the centralized computer system or other similar centralized controller when a quantity of particulate matter from the interior cavity of the housing exceeds a threshold. The threshold can be set by to ensure that dirty or malfunctioning filtration system do not their respective pill dispensing devices or the facility in general.

An Exemplary Method for Dispensing Pills

Figure 23:
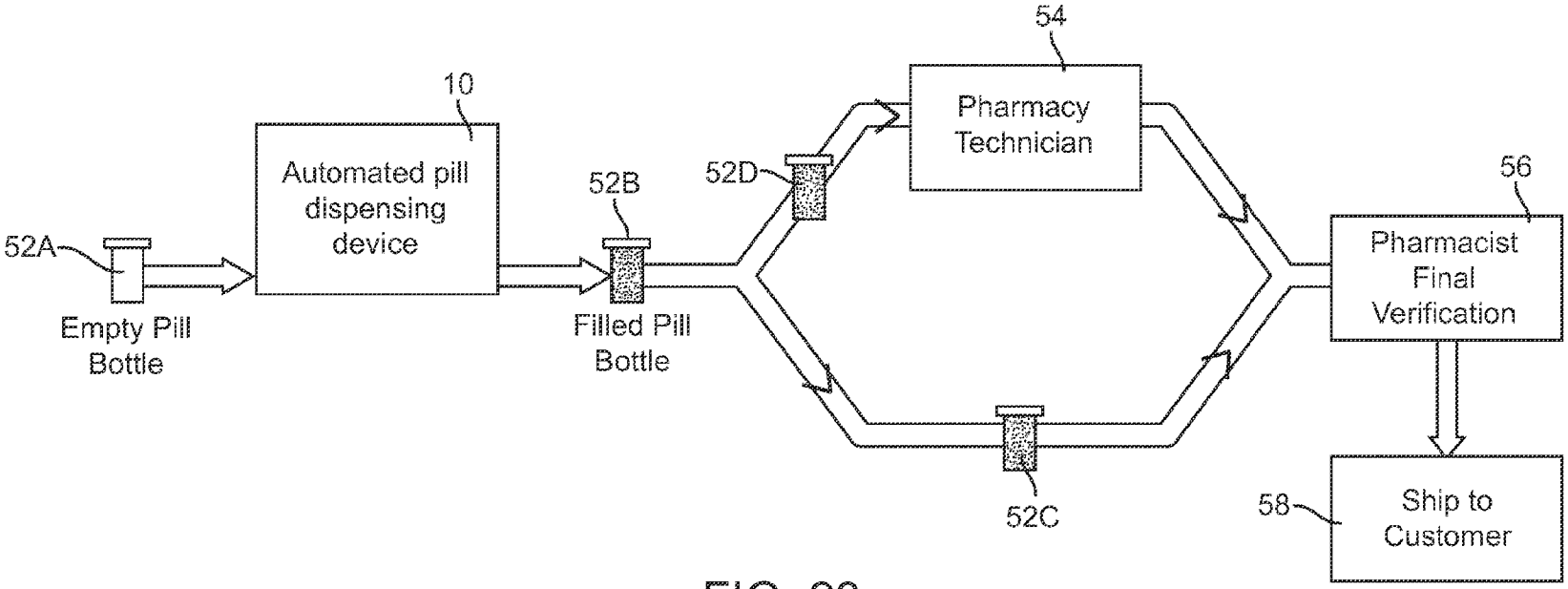
FIG. 23 is a flow chart illustrating a method of dispensing pills with one or more pills dispensing devices according to an embodiment.

FIG. 23 is a flow chart illustrating a method of dispensing pills with one or more pills dispensing devices according to an embodiment. Most often the method is performed with a bank of pill dispensing devices and a centralized computer system. The centralized computer system or other similar centralized controller schedules the prescription for fulfillment within an automated pill dispensing facility. The automated pill dispensing facility typically comprises comprising two or more pill dispensing devices in arranged in an array configuration. The array configuration generally encompasses two or more banks or rows of pill dispensing devices typically but not necessarily with each bank or row having the same number of pill dispensing devices therein. Each of the pill dispensing devices may contain a different prescription drug. However, there can and typically is more than one pill dispensing device that contains and dispenses the same drug type or pill.

A general method of fulfilling a prescription using two or more pill dispensing device is described herein. Initially, the prescription is typically received by a pharmacy and is entered into the pharmacy's order entry or information system. The prescription includes at least a type and a quantity of pills that is entered. The pharmacy's order entry or information system will typically be in communication with the centralized computer system associated with the automated pill dispensing facility. Next, the centralized computer system schedules the prescription for fulfillment. Alternatively, the prescription may be communicated by another means and directly entered into the centralized computer system to schedule the prescription for fulfillment Next, an empty pill bottle 52a is routed to the appropriate dispensing device 10 typically on a conveyor line of a conveyor belt system operatively coupled to the centralized computer system. The empty pill bottle 52a is positioned directly underneath the dispensing neck of the appropriate pill dispensing device. The centralized computer signals the controller of the appropriate pill dispensing device to deposit a predetermined number of pills into the empty pill bottle 52a.

Next, the pill dispensing device's controller activates a feeding assembly (typically a vibratory base unit), a plurality or optical sensors, and a filtration system if so equipped. The pills advance up a spiraling edge of a vibratory feeding bowl and pass through a singulator. Proceeding in a generally single file manner, each pill falls one by one off an exit edge of the vibratory feeding bowl into an upper portion of a pill dispensing route. As the pills pass through the upper portion, they also pass through the light beams provided by a first and second sensor pairs. Then the pills continue down through a lower portion of the dispensing route, usually a dispensing chute. After passing through the dispensing chute, the pills pass through a dispensing neck and out of the pill dispensing device and into the pill bottle. Once the desired number of pills has been dispensed, the controller signals the vibratory base unit to turn off. Moreover, a pill stop mechanism is activated by the controller to prevent any additional pills located close to the exit edge from falling into the upper portion of the dispensing route. If so equipped, the filtration system is also deactivated by the controller. Count information concerning the particular count recorded by each optical sensor is sent to the centralized computer system. Based on the information and data received from the optical sensors, the centralized computer routes the now filled pill bottle 52b.

In most circumstances, both optical sensors will count the correct number of pills. In some embodiments, this has been measured to occur approximately 99.5% of the time. While correctly filled pill bottle 52c will then be routed directly to a pharmacist station 56 for final verification. Typically, the pharmacist will verify that the pills contained in the filled pill bottle 52c match those specified on the label and/or are for the described patient. Once the verification is complete, the filled pill bottle 52c bottle is shipped to a shipping address of a customer or designated location as indicated in block 58.

In another circumstance, the optical sensors indicate disparate readings. For example, where the desired count is 90, a first sensor pair might indicate 91 pills, whereas, a second optical sensor might indicates 90 pills. As a general rule, the controller of the pill dispensing device does not (or attempts not to) permit undercounting and under dispensing of pills. As such, if enough pills are available within the pill dispensing device, the controller will always continue operation until the count indicated by the optical sensor having the lower count matches the desired count. If a system error or counting anomaly occurs a user or operator can make routing decisions based on those anomalies (e.g., sensor mismatch, known over-count, etc.).

However, depending on the value of the pills and the cost to have a technician perform a manual recount, the centralized computer system will either (i) route the mismatched count pill bottle 52D to a technician station for recounting as indicated in box 54, or (ii) route the correct count pill bottle 52c to the pharmacist station 56 for final verification. The logic in the centralized computer system will typically be programmed to make that determination based on the type of pill and optionally the amount/quantity of the optical sensor mismatch or other counting errors.

In operation, there are several reasons why a sensor mismatch can occur. Two pills may have fallen into the chute at approximately the same time but were positioned in such a fashion as to register a single count with one optical sensor and differently positioned when passing through the other optical sensor or sensors as to register a count for each pill. In the case of a broken pill or pill fragment the orientation of the fragment when passing through the light beams of each pair of sensor heads of the optical sensors can cause one light beam to register a count while the other one or ones failing to do so. The tolerance level wherein a fragment is counted can be adjusted especially for the particular pill dispensing devices that are dispensing pills with a high potential for breakage. In addition, stray debris within a temporary storage compartment or elsewhere in the pill dispensing device such as, but not limited to, stray cotton, broken desiccant, and other material can contribute to a sensor mismatch. Finally, continued sensor mismatches from the same pill dispensing device can indicate a problem with at least one of the optical sensors in the pill dispensing device. Accordingly, the centralized computer system can be configured to maintain a log as well as generate an alarm relating to the performance of each pill dispensing to determine whether maintenance or repair is required.

A third circumstance occurs when both sensors indicate the same numerical count and the count exceeds the desired count. A known over-count typically occurs when a pill falls off of the vibratory feeder bowl's exit edge after the desired count has been complete and the controller has sent a stop command to the feeding assembly. This often will depend on the particular settings of the vibratory base unit. When the vibratory base unit is set to a more aggressive or higher level of vibration, the risk of having multiple pills fall off the exit edge nearly contemporaneously is increased. However, if the level of vibration is reduced or low, the speed at which the pill bottle is filled is often reduced. As a middle ground, the pill dispensing device can be set to maintain a high level of vibration for majority of the count but slow down to a more controlled level of vibration for the last few pills in the desired count. A known over-count indication is treated in much the same manner as a sensor mismatch indication. Namely, the determination whether to have a pharmacy technician manually verify the count is often dependent upon the value of the particular pills.

In some circumstances, such as when a hopper or the temporary storage compartment is empty, the pill dispensing device may not be capable of providing the desired or predetermined count. Typically, the controller of the pill dispensing device will have a timeout feature that will shut down the device and signal the centralized computer system that something is wrong if the desired or predetermined count is not achieved after a preset or predetermined period of time. In other instances where the mismatch between two sensors becomes too great, the controller is also configured to abort the specific count and signal a centralized computer system of the sensor mismatch. In one variation, this occurs when the mismatch between two optical sensors exceeds three.

An Exemplary Pill Dispensing System and Computer System for Use Therewith

Figure 24:
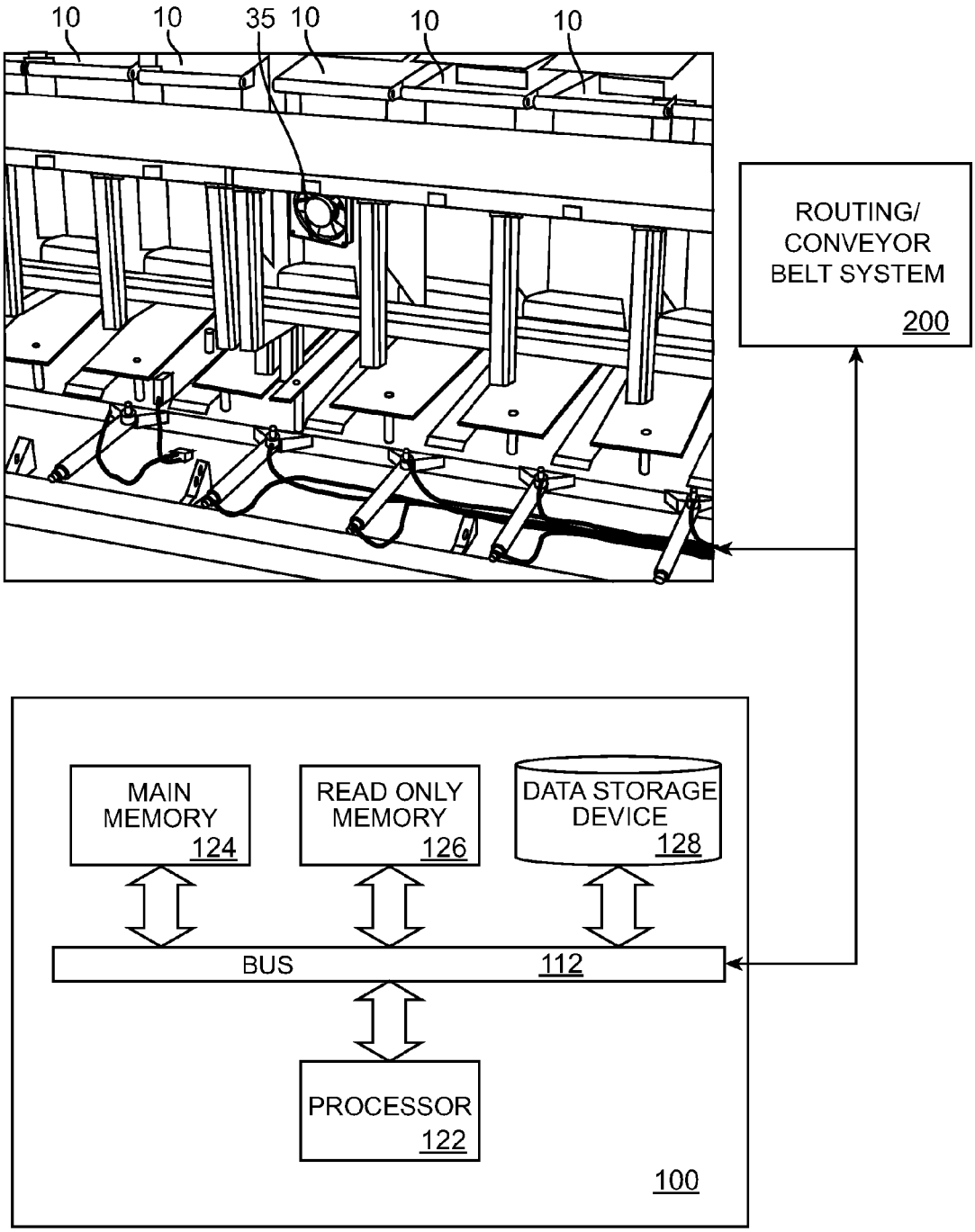
FIG. 24 is a block diagram of an exemplary computer system as incorporated into a pill dispensing system utilizing two or more pills dispensing devices according to an embodiment.

Now referring to FIG. 24, the block diagram of an exemplary general purpose computer system as incorporated into a pill dispensing system utilizing two or more pills dispensing devices is illustrated according to an embodiment. It is to be appreciated that embodiments of the pill dispensing system typically utilize embodiments of the exemplary pill dispensing device illustrated in FIGS. 1-22 and exemplary method of dispensing pills illustrated in FIG. 23 along with the complete disclosure herein.

Computer system 100 is an exemplary general purpose computer system upon which embodiments of the present invention can be implemented. Computer system 100 typically comprises a bus or other communications means 112 for communicating data or information, and a processing means such as a processor 122. The computer system 100 further comprises a random access memory (RAM) or other similar dynamically-generated data storage device 124 (referred to as main memory in FIG. 24 and hereinafter). Main memory 124 is coupled to the bus 112 for storing information and instructions to be executed by the processor 122. Additionally, the main memory 124 can be used for storing temporary variables or other intermediate information during execution of instructions by the processor 122.

Computer system 100 also comprises a read only memory (ROM) and/or other static storage device 126 coupled to the bus 112 for storing static information and instructions for the processor 122. A data storage device 128 such as, but not limited to, a solid state drive or an optical disk drive can also be coupled to the bus 112 as a component of the computer system 100 for storing data and instructions.

A plurality of devices can be coupled to computer system 100 via the bus 112. An output or display device, such as but not limited to a cathode ray tube (CRT) on liquid crystal display (LCD) may be provided for displaying information to a user. Typically, an input device such as an alphanumeric keyboard, including alphanumeric, symbol, and other keys can be coupled to the bus 112 for communicating information and/or command selections to the processor 122. Another type of user input device, such as a mouse, trackball, or cursor direction keys for communicating information and/or command selections to the processor 122 can be utilized for controlling cursor movement on the display device.

Moreover, computer system 100 can also include a communications device or interface operatively coupled via the bus 122 allowing data and/or software to be transferred between computer system 100 and external networks and devices. Examples of communications devices include, but are not limited to a modem, a network interface card, a wireless network interface card, a serial concentrator, or other well-known interface device, such as those used for Ethernet, token ring, asynchronous transfer mode (ATM), or other types of physical attachment for purposes of providing a communications link to support a local or wide area network. In this manner, computer system 100 can be coupled to one or more order entry or information systems, such as those used by a pharmacy or other medication administration entity via a conventional network infrastructure, such as and intranet and/or the Internet, for example. Moreover, in one exemplary embodiment, pill dispensing devices communicate with the computer system 100 though a 16-32 port serial concentrator coupled to the bus 112.

It is appreciated that a lesser or more equipped computer system than the example described above can be desirable for certain implementations of the system of the present invention. Therefore, the configuration of the computer system 100 will vary from implementation to implementation depending on numerous factors such as price constraints, performance requirements, technological improvements, and/or other circumstances. It is pertinent to note that, while the operation described herein can be performed under the control of a programmed processor, such as the processor 122 in FIG. 24, in alternative embodiments, the operations can be fully or partially implemented by any programmable or hard-coded logic, such as but not limited to field programmable gate arrays (FPGAs), TTL logic, application specific integrated circuits (ASICs), for example.

Additionally, the exemplary methods of the embodiments can be performed by any combination of programmed general purpose computer components and/or custom hardware components. Therefore, nothing disclosed herein should be construed as limiting the present invention to a particular embodiment wherein the recited operations are performed by a specific combination of hardware components. As would be obvious to one skilled in the art of computer science and systems engineering, many variations and alternate embodiments of the systems described above can be used with embodiments of the present invention. The plurality of systems and software modules can be stored in any one of a number of internal and external storage devices, remotely or centrally located, as those of skill in the art could easily adapt one embodiment computer architecture to a multitude of embodiments. Furthermore, a system for making, using, or selling the embodiments can be one or more processing systems including, but not limited to, servers, a central processing unit, memory, storage devices, input/output devices, communication links and devices, or any modules or components of the one or more processing system including by way of example, but not limitation, software, firmware, hardware, or any combination thereof.

Still referring to FIG. 24, the computer system 100 is coupled to two or more pill dispensing devices 10 and a routing or conveyor belt system 200 via the bus 112. The routing or conveyor belt system 200 is adapted to route pill bottle to the two or more pill dispensing devices 10 and to various stations, such as a technician's station, a pharmacist's station, and a station or staging area for shipping the pill bottles. The computer system 100 typically controls the operation of the routing or conveyor belt system 200, however, embodiments are contemplated where the routing or conveyor belt system 200 includes its own controlling system with which the computer system 100 may or may not interface.

Routing decision relating to the pill bottles into which pill have been dispensed are typically based on several types of conditions occurring during the dispensing process of each pill dispensing device 10 and the count information from the plurality of optical sensors therein. A sensor mismatch occurs when the number of pills counted by at least one of the plurality of optical sensors is different than the number of pills counted by another of the plurality of optical sensors. For example, the first optical sensor counted 90 pills and the second optical sensor counted 91 pills dispensed into the pill bottle.

A known over-count occurs when: (i) the number of pills counted by each of the plurality of optical sensors is the same, and (ii) the number of pills counted each of the plurality of optical sensors is greater than a predetermined number. The predetermined number is the number ordered or entered for the fulfillment of the prescription. For example, the prescription calls for 90 pills and hence a pill bottle is scheduled to be filled by the appropriate pill dispensing machine accordingly (the predetermined number is 90). The first optical sensor counted 91 pills and the second optical sensor counted 91 pills dispensed into the pill bottle. Hence a known over-count has occurred.

An abort count sensor mismatch occurs when the number of pills counted by at least one of the plurality of optical sensors is different than the number of pills counted by another of the plurality of optical sensors by a specific number. The specific number can be and typically is programmable. For instance, the specific number can be 3 thereby generating abort count sensor mismatch when there is a disparity of three or more between the optical sensors. For example, if the specific number is 3, and if the first optical sensor counted 90 pills and the second optical sensor counted 95 pills dispensed into the pill bottle; then an abort count sensor mismatch has occurred.

A known under-count occurs when: (i) the number of pills counted by each of the plurality of optical sensors is the same, and (ii) the number of pills counted each of the plurality of optical sensors is less than the predetermined number. For example, the prescription calls for 90 pills and hence a pill bottle is scheduled to be filled by the appropriate pill dispensing machine accordingly (the predetermined number is 90). The first optical sensor counted 65 pills and the second optical sensor counted 65 pills dispensed into the pill bottle. Hence a known under-count has occurred.

It is to be appreciated in some embodiments the controller of the pill dispensing device 10 and processor and memory therein will provide the logic, compare, and generate sensor mismatch, known over-count, abort count sensor mismatch, and known under-count indications. Additionally, in such embodiments, the controller of the pill dispensing device 10 can be adapted to send information, data, and alarm to the computer system 100 related to these indications. In other embodiments, the sensor mismatch, known over-count, abort count sensor mismatch, and known under-count indications may be performed, compared, and generated by the computer system 100.

Alternate Embodiments and Variations

Alternate embodiments and variations thereof described above are merely exemplary and are not meant to limit the scope of the present invention. It is to be appreciated that numerous alternate embodiments and variations to the system and method described herein have been contemplated as would be obvious to one of ordinary skill in the art with the benefit of this disclosure. For example, alternative embodiments of the automated pill dispensing device may be adapted to dispense, count, and/or package various items or objects such as, but not limited to, coins, tokens, chips, bolts, fasteners, and candy.

Moreover, methods of various embodiments can be implemented: as a sequence of computer-implemented steps running on the system; and/or as interconnected modules within the system. Methods of various embodiments can be implemented on a special purpose computer, a general purpose computer programmed with software designed to execute the processes described herein, and/or a computer-readable storage medium. Furthermore, it is understood that embodiments of the present invention are not limited with regard to any particular network environment or the application used to communicate in that environment. The implementation of the systems and methods of the medication reconciliation system is a matter of choice dependent on the particular performance requirements of the system implementing the methods of the present invention as well as the computer and networking resources available in a given scenario.

It will be recognized by one of ordinary skill in the art that the operations steps and modules can be implemented in software, and firmware, in special-purpose digital logic, analog circuits, and any combination thereof without deviating from the spirit and scope of the present invention as recited within the claims attached hereto. All variations of the invention that read upon the appended claims are intended and contemplated to be within the scope of the present invention.

I claim:

[1. A pill dispensing device comprising:

a temporary storage compartment adapted to store one or more pills;

a feeding assembly including a singulator, the feeding assembly being coupled to the temporary storage compartment and adapted to move and stop the one or more pills;

a dispensing route operatively coupled to an exit position of the feeding assembly and disposed to receive the one or more pills;

a plurality of optical sensors, each optical sensor being adapted to produce a light beam and indicate a count signal for each of the one or more pills that disrupt the light beam, the light beam being disposed within a portion of the dispensing route;

a controller coupled to the feeding assembly and the plurality of optical sensors;

a housing enclosing at least the feeding assembly, the portion of the dispensing route, and the plurality of optical sensors;

a filtration assembly configured to remove air and particulate matter from an interior cavity of the housing; and wherein:

the controller is programmable with a specific number of sensor mismatches;

the controller is configured to receive count signals from each of the plurality of optical sensors, the count signal indicating that a pill has disrupted the light beam;

the controller is configured to generate an abort count sensor mismatch indication when the number of pills counted by at least one of the plurality of optical sensors is different than the number of pills counted by another of the plurality of optical sensors by the specific number;

the controller is configured to send a stop instruction to the feeding assembly based on the abort count sensor mismatch indication; and the feeding assembly is adapted to stop moving the one or more pills upon receiving the stop instruction from the controller.]

[2. The pill dispensing device of claim 1, wherein:

the feeding assembly is adapted to vibrate at a plurality of speeds and includes a vibratory base unit, a vibratory feeder bowl; and the singulator is configured to separate stacked pills.]

[3. The pill dispensing device of claim 2, wherein the dispensing route comprises, a dispensing chute having, an upper portion proximate and operatively coupled to the exit position of the feeding assembly, the upper portion allowing the light beam of each optical sensor therein to project, and a lower portion configured to change the direction of the one or more pills, and a dispensing neck coupled to the lower portion of the dispensing chute and adapted to fit over a pill bottle.]

[4. The pill dispensing device of claim 3, wherein the portion of the dispensing neck is extended and retracted by one or more pneumatic actuators.]

[5. The pill dispensing device of claim 2, wherein the feeding assembly further includes a stopping mechanism coupled to the vibratory feeder bowl proximal the exit position, and the singulator is adjustable for pills of a particular size.]

[6. A method for filling a prescription using two or more of the pill dispensing device of claim 1, the method comprising:

scheduling a prescription for fulfillment, the prescription including at least a type and a quantity of pills, the scheduling including at least entering the quantity of pills into a computer system, the computer system being in communication with each controller of the two or more pill dispensing devices;

programming the specific number of abort count sensor mismatches by entering a specific number of sensor mismatches into the computer system;

routing a pill bottle proximal a first pill dispensing device of the two or more pill dispensing devices, the first pill dispensing device having a plurality of the type of pills as the one or more pills in its temporary storage compartment and an opening of the pill bottle being substantially aligned with a dispensing end of the dispensing route of the first pill dispensing device;

signaling, by the computer system, the first pill dispensing device with at least a predetermined number of pills according to the prescription quantity of pills;

activating the feeding assembly and the plurality of optical sensors of the first pill dispensing device;

counting each pill of the plurality of the type of pills using each of the plurality of optical sensors; and deactivating the feeding assembly when each of the plurality of optical sensors has counted a number of pills equal to the predetermined number.]

[7. The method of claim 6, wherein the two or more pill dispensing devices are arranged in an array configuration.]

[8. The method of claim 7, wherein the filtration assembly is adapted to transmit an alarm to the computer system when a quantity of particulate matter from an interior of the at least one pill dispensing device exceeds a threshold.]

[9. A method for filling a prescription using the pill dispensing device of claim 1 wherein the controller includes a controller interface panel, the method comprising:

entering at least a quantity of pills indicated by a prescription into the controller interface panel;

programming the specific number of sensor mismatches by entering the specific number of sensor mismatches into the controller interface panel;

placing a pill bottle proximal the pill dispensing device, the pill dispensing device having a plurality of pills in its temporary storage compartment and an opening of the pill bottle being substantially aligned with a dispensing end of the dispensing route;

activating, by the controller, the feeding assembly and the plurality of optical sensors of the pill dispensing device;

counting, by the controller, each of the plurality of pill count signals indicated by each of the plurality of optical sensors; and deactivating, by the controller, the feeding assembly when each of the plurality of optical sensors has indicated a number of pills equal to the quantity of pills entered.]

*10. A pill dispensing device comprising:*

*a temporary storage compartment adapted to store one or more pills;*

*a feeding assembly that comprises at least one singulator and that is coupled to said temporary storage compartment;*

*a dispensing route coupled to an exit position of said feeding assembly and disposed to receive said one or more pills;*

*a plurality of sensors, each sensor adapted to indicate a count signal for each of said one or more pills that moves along at least a portion of said dispensing route;*

*a controller coupled to said feeding assembly and said plurality of sensors;*

*a housing enclosing at least said feeding assembly, said portion of said dispensing route, and said plurality of sensors; and*

*a filtration assmbly configured to remove air and particulate matter from an interior cavity of said housing;*

*wherein:*

*said controller is configured to be programmable with a specific number of sensor mismatches,*

*said controller is configured to receive said count signals from each of said plurality of sensors and to record a sensor mismatch when, during counting for a prescription, a pill count of one of said sensors is different from a pill count of another of said sensors,*

*said controller is configured to generate an abort count sensor mismatch indication when a difference between said pill count of said one of said sensors and said pill count of said another of said sensors reaches said specific number of sensor mismatches, and*

*said controller is configured to send a stop instruction to the feeding assembly based on said abort count sensor mismatch indication.*

*11. The pill dispensing device of claim 10 wherein said feeding assembly is adapted to vibrate at a plurality of speeds and includes a vibratory base unit and a vibratory feeder bowl; and wherein said singulator is configured to separate stacked pills.*

*12. The pill dispensing device of claim 10 wherein said dispensing route comprises*

*a dispensing chute having:*

*an upper portion coupled to said exit position of said feeding assembly, the upper portion allowing said one or more of said plurality of said sensors therein to sense,*

*a lower portion configured to change the direction of said one or more pills, and*

*a dispensing neck coupled to said lower portion of said dispensing chute and adapted to be positioned over a pill container.*

*13. The pill dispensing device of claim 12, further comprising one or more pneumatic actuators configured to extend and to retract at least one portion of said dispensing neck.*

*14. The pill dispensing device of claim 10, wherein said feeding assembly further comprises a stopping mechanism coupled to said vibratory feeder bowl proximal the exit position, and the singulator is adjustable for pills of a particular size.*

*15. The pill dispensing device of claim 10, wherein said sensors comprise an optical sensor.*

*16. The pill dispensing device of claim 10, wherein said sensors comprise a fiber-optic sensor.*

*17. The pill dispensing device of claim 10, wherein said sensors comprise an infrared sensor.*

*18. The pill dispensing device of claim 10, wherein said sensors comprise an ultraviolet sensor.*

*19. The pill dispensing device of claim 10, wherein said plurality of sensors comprises a plurality of different types of sensors.*

*20. The pill dispensing device of claim 10, and further comprising a computer system programmed to log one or more pill count discrepancy.*

*21. The pill dispensing device of claim 20, wherein said one or more pill count discrepancy comprises at least one of a sensor mismatch discrepancy, a known over-count discrepancy, or a known under-count discrepancy.*

*22. The pill dispensing device of claim 10, further comprising a computer system configured to reroute a pill container for a recount as a result of said abort count sensor mismatch indication.*

*23. The pill dispensing device of claim 10, further comprising a computer system configured to log performance associated with sensor mismatches.*

*24. The pill dispensing device of claim 10 further comprising a computer system configured to communicate to an end user a sensor mismatch indication when said sensor mismatch is recorded by said controller.*

*25. The pill dispensing device of claim 10 wherein one or more of said sensors is adapted to communicate an alarm to a computer system when a quantity of particulate matter from an interior of the pill dispensing device exceeds a threshold.*

*26. The pill dispensing device of claim 10 wherein one or more of said sensors is configured to communicate a stop instruction to a computer system to stop movement of said pills along said dispensing route.*

* * * * *